(12) United States Patent
Southern

(10) Patent No.: US 8,518,649 B2
(45) Date of Patent: *Aug. 27, 2013

(54) SYSTEMS AND METHODS FOR ANALYZING PERSISTENT HOMEOSTATIC PERTURBATIONS

(76) Inventor: Šárka O. Southern, San Diego, CA (US)

( * ) Notice: Subject to any disclaimer, the term of this patent is extended or adjusted under 35 U.S.C. 154(b) by 187 days.

This patent is subject to a terminal disclaimer.

(21) Appl. No.: 12/282,840

(22) PCT Filed: Apr. 4, 2008

(86) PCT No.: PCT/US2008/004448
§ 371 (c)(1), (2), (4) Date: Apr. 5, 2010

(87) PCT Pub. No.: WO2008/124096
PCT Pub. Date: Oct. 16, 2008

(65) Prior Publication Data
US 2010/0203563 A1    Aug. 12, 2010

Related U.S. Application Data

(60) Provisional application No. 60/910,158, filed on Apr. 4, 2007.

(51) Int. Cl.
*G01N 33/53* (2006.01)

(52) U.S. Cl.
USPC ............................... 435/7.1; 436/518

(58) Field of Classification Search
None
See application file for complete search history.

(56) References Cited

U.S. PATENT DOCUMENTS

| 4,959,306 | A  | * | 9/1990  | Kameda et al. ........... 435/7.92 |
| 5,980,954 | A  | * | 11/1999 | Bolton ..................... 424/613 |
| 6,965,023 | B2 |   | 11/2005 | Reed et al. |
| 2002/0090620 | A1 |   | 7/2002  | Davis et al. |
| 2003/0165983 | A1 |   | 9/2003  | Gibson et al. |
| 2005/0221421 | A1 | * | 10/2005 | Tran et al. ............... 435/69.1 |
| 2007/0020695 | A1 |   | 1/2007  | Boux et al. |

OTHER PUBLICATIONS

Hamler et al. (Proteomics 2004 vol. 4, p. 562-577).*
Kregel et al. (J. Appl. Physiol. 2002 vol. 92, p. 2177-2186).*
Dori et al., "ARP, the Cleavable C-Terminal Peptide of "Readthrough" Acetylcholinesterase, Promotes Neuronal Development and Plasticity", *J Mol Sci*, 28:247-256, 2006.

* cited by examiner

*Primary Examiner* — Jacob Cheu
(74) *Attorney, Agent, or Firm* — DLA Piper LLP (US)

(57) ABSTRACT

This invention is in the field of homeostasis analysis. More particularly, it relates to systems and methods for analyzing persistent homeostatic perturbations, i.e. chronic stress, by measuring levels of biomarkers that are related to chronic stress. This invention is also directed to systems and methods for analyzing the molecular mechanisms of chronic stress.

8 Claims, 13 Drawing Sheets

Principle of the Stress Response Profiling Method

FIGURE 2

SR Biomarkers: Association with SR Pathways and Expression in Taxonomic Groups of Organisms

| # | SR biomarker | Abbreviated name | Expression | | | | | SR pathways | | | | | | | | | |
|---|---|---|---|---|---|---|---|---|---|---|---|---|---|---|---|---|---|
| | | | A | B | C | D | E | 1 | 2 | 3 | 4 | 5 | 6 | 7 | 8 | 9 | 10 |
| 1 | Beta-endorphin | Endorphin | + | + | + | | | 0 | 0 | 0 | 0 | 0 | 1 | 1 | 1 | 1 | 0 |
| 2 | Caspase 8 | Caspase 8 | + | + | + | | | 0 | 0 | 0 | 0 | 0 | 0 | 0 | 0 | 1 | 0 |
| 3 | Cyclin D1 | Cyclin | + | + | + | | | 0 | 0 | 0 | 1 | 0 | 1 | 1 | 1 | 0 | 0 |
| 4 | Cyclooxygenase 2 | Cox-2 | + | + | + | | | 1 | 0 | 0 | 0 | 0 | 1 | 1 | 0 | 0 | 0 |
| 5 | Cytochrome P 450 | CYP450 | + | + | + | + | + | 1 | 1 | 0 | 0 | 0 | 1 | 1 | 1 | 1 | 0 |
| 6 | Cytoplasmic cytochrome c | Cyt c | + | + | | | | 0 | 0 | 0 | 0 | 0 | 1 | 1 | 0 | 0 | 0 |
| 7 | Epidermal growth factor receptor | EGFR | + | + | + | | | 1 | 0 | 1 | 0 | 1 | 1 | 1 | 1 | 1 | 0 |
| 8 | Ferritin | Ferritin | + | + | + | + | + | 1 | 0 | 0 | 0 | 0 | 0 | 1 | 1 | 1 | 1 |
| 9 | Glucocorticoid receptor | GR | + | | | | | 1 | 1 | 0 | 0 | 0 | 1 | 1 | 1 | 1 | 0 |
| 10 | Glucose regulated protein Grp58 | Grp58 | + | + | | | + | 1 | 1 | 1 | 0 | 0 | 1 | 1 | 0 | 0 | 0 |
| 11 | Glucose regulated protein Grp75 | Grp75 | + | + | + | + | + | 1 | 0 | 1 | 0 | 0 | 0 | 0 | 0 | 1 | 0 |
| 12 | Glutathione-S-transferase p | GST | + | + | + | + | + | 1 | 1 | 0 | 1 | 0 | 1 | 1 | 1 | 1 | 0 |
| 13 | Heat shock protein 25/27 | Hsp25/27 | + | + | + | + | + | 1 | 1 | 0 | 0 | 1 | 0 | 1 | 0 | 1 | 1 |
| 14 | Heat shock protein 40 | Hsp40 | + | + | + | + | + | 0 | 0 | 1 | 0 | 0 | 1 | 1 | 1 | 1 | 0 |
| 15 | Heat shock protein 60 | Hsp60 | + | + | + | + | + | 0 | 1 | 1 | 0 | 0 | 1 | 0 | 1 | 1 | 0 |
| 16 | Heat shock protein 90 | Hsp90 | + | + | + | + | + | 1 | 1 | 1 | 1 | 1 | 1 | 1 | 1 | 1 | 0 |
| 17 | Heat shock transcription factor HSF-1 | HSF-1 | + | + | | | | 1 | 1 | 1 | 0 | 0 | 1 | 1 | 0 | 1 | 0 |
| 18 | Heme oxygenase-1 | HO-1 | + | + | | | | 1 | 0 | 0 | 1 | 1 | 1 | 1 | 1 | 1 | 0 |
| 19 | Interleukin IL-1beta | IL-1 | + | + | + | | | 0 | 0 | 0 | 0 | 0 | 1 | 1 | 1 | 1 | 0 |
| 20 | Interleukin IL-6 | IL-6 | + | + | + | | | 1 | 0 | 1 | 0 | 0 | 1 | 0 | 0 | 0 | 1 |
| 21 | Interleukin IL-8 | IL-8 | + | + | | | | 0 | 0 | 0 | 0 | 1 | 1 | 1 | 1 | 1 | 0 |
| 22 | Interleukin IL-10 | IL-10 | + | | | | | 0 | 0 | 0 | 0 | 0 | 1 | 0 | 0 | 1 | 1 |
| 23 | Interleukin IL-12 | IL-12 | + | | | | | 0 | 0 | 0 | 0 | 1 | 1 | 1 | 1 | 1 | 1 |
| 24 | Laminin | Laminin | + | + | | | | 1 | 1 | 0 | 0 | 1 | 1 | 1 | 1 | 1 | 0 |
| 25 | Leptin receptor | Leptin R | + | | | | | 0 | 0 | 0 | 0 | 0 | 1 | 1 | 1 | 1 | 0 |

FIG. 2, continued

| # | SR biomarker | Abbreviated name | Expression ||||| SR pathways ||||||||||
|---|---|---|---|---|---|---|---|---|---|---|---|---|---|---|---|---|
| | | | A | B | C | D | E | 1 | 2 | 3 | 4 | 5 | 6 | 7 | 8 | 9 | 10 |
| 26 | Metallothionein | MT | + | + | + | + | + | 1 | 0 | 0 | 1 | 0 | 1 | 1 | 1 | 1 | 1 |
| 27 | Stress-activated MAP kinase Mekk-1 | Mekk-1 | + | + | + | + | + | 0 | 0 | 0 | 0 | 1 | 1 | 1 | 0 | 1 | 1 |
| 28 | Mitogen activated MAP kinase Mek-1 | Mek-1 | + | + | + | + | + | 0 | 0 | 0 | 1 | 1 | 1 | 1 | 1 | 1 | 0 |
| 29 | NADPH-cytochrome P 450 reductase | CYP red | + | + | + | | + | 1 | 1 | 0 | 0 | 0 | 1 | 1 | 1 | 1 | 0 |
| 30 | Nitric oxide synthase II, inducible | iNOS | + | + | + | | + | 1 | 0 | 0 | 0 | 1 | 1 | 1 | 1 | 1 | 1 |
| 31 | Proto-oncogene c-Fos protein | Fos | + | + | + | | | 0 | 0 | 0 | 0 | 1 | 1 | 1 | 1 | 1 | 0 |
| 32 | Proto-oncogene c-Jun protein | Jun | + | + | + | | + | 0 | 0 | 0 | 0 | 0 | 1 | 1 | 1 | 1 | 0 |
| 33 | Serotonin receptor | Serotonin R | + | + | + | | + | 1 | 0 | 0 | 0 | 1 | 1 | 1 | 0 | 1 | 0 |
| 34 | Serotonin | Serotonin | + | + | + | | | 0 | 0 | 0 | 0 | 1 | 1 | 1 | 0 | 1 | 0 |
| 35 | Substance P | Substance P | + | + | | | | 0 | 0 | 0 | 0 | 1 | 1 | 0 | 0 | 1 | 0 |
| 36 | Superoxide dismutase Mn | SOD Mn | + | + | + | + | + | 1 | 0 | 0 | 1 | 1 | 1 | 1 | 1 | 1 | 1 |
| 37 | Superoxide dismutase Cu/Zn | SOD Cu/Zn | + | + | + | + | | 1 | 0 | 0 | 1 | 1 | 1 | 1 | 1 | 1 | 1 |
| 38 | Transforming growth factors beta -1,2,3 | TGF | + | + | + | | + | 0 | 0 | 0 | 0 | 0 | 0 | 1 | 1 | 1 | 1 |
| 39 | Tumor suppressor p53 | p53 | + | + | + | | | 0 | 0 | 0 | 1 | 0 | 1 | 1 | 0 | 0 | 1 |
| 40 | Vasoactive intestinal peptide | VIP | + | + | | | | 0 | 0 | 0 | 0 | 0 | 1 | 0 | 1 | 1 | 0 |

FIGURE 3

SR Biomarkers: Association with SR Pathways

| # | SR biomarker | Abbreviated name | 1 | 2 | 3 | 4 | 5 | 6 | 7 | 8 | 9 | 10 |
|---|---|---|---|---|---|---|---|---|---|---|---|---|
| 41 | Heat shock protein 70 | Hsp70 | | | + | + | + | + | | | + | |
| 42 | Metalloproteinase 9 | MMP-9 | | | | | + | | | | | |
| 43 | Fibronectin | Fibronectin | | | | | + | | | | | |
| 44 | Collagen | Collagen | | | | | + | | | | | |
| 45 | Cadherins | E-cad, Pan-cad | | | | | + | + | | | | |
| 46 | Cell adhesion molecules | I-CAM, V-CAM, N-CAM | | | | | + | | | | + | |
| 47 | E-selectin | E-selectin | | | | | + | | | | | |
| 48 | Monocyte chemotactic protein 1 | MCP-1 | | | | | + | | | | + | |
| 49 | Calmodulin | CaM | | | | | + | + | | + | + | |
| 50 | Integrins alpha, beta | Integrin | | | | | + | | | | + | |
| 51 | DNA damage binding protein-2 | DDB2 | | | | + | | | | | | |
| 52 | Xeroderma pigmentosum (XP) C protein | XPC | | | | + | | | | | | |
| 53 | DNA glycosylase OGG1 | OGG1 | | | | + | | | | | | |
| 54 | pyrimidine-base DNA glycosylases NEIL-1, 2 (nei) | NEIL | | | | + | | | | | | |
| 55 | uracil DNA glycosylase UNG (Ung) | UNG | | | | + | | | | | | |
| 56 | thymidine DNA glycosylase TDG (Mug) | TDG | | | | + | | | | | | |
| 57 | DNA glycosylase MYH (MutY) | MYH | | | | + | | | | | | |
| 58 | DNA glycosylase MTH1 | MTH1 | | | | + | | | | | | |
| 59 | Apurinic/Apyrimidinic endonuclease | APE | | | | + | | | | | | |
| 60 | MSH-2 | MSH-2 | | | | + | | + | + | | | |
| 61 | MLH-1 | MLH-1 | | | | + | | + | + | | | |
| 62 | Senescence-associated beta-galactosidase | SA-beta-gal | | | | + | | + | + | | | |
| 63 | p21 | p21 | | | | + | | + | + | | | |
| 64 | 8-hydroxy-deoxyguanosine | 8-OH-dG | | | | + | | | | | | |
| 65 | 8-hydroxy-guanine | 8-OH-G | | | | + | | | | | | |
| 66 | Peripheral benzodiazepine receptor | PBR | | | | | | | + | + | + | + |
| 67 | Toll-like receptor | TLR | | | | | | | | | + | + |
| 68 | Bacterial TspO protein | TspO | | | | | | | | | | + |
| 69 | Bacterial protease DegP | DegP | | | | | | | | | | + |
| 70 | Bacterial SOD Fe | SOD Fe | + | | | | | | | | + | + |
| 71 | Bacterial glutathione reductaseA | gorA | | + | | | | | | | | + |
| 72 | Bacterial alkyl hydroperoxide reductase | ahp | | + | | | | | | | | + |
| 73 | Bacterial ferric uptake regulator | fur | + | | | | | | + | | | + |

FIG. 3, continued

| #  | SR biomarker | Abbreviated name | \multicolumn{10}{c}{SR pathways} |||||||||||
|----|--------------|------------------|---|---|---|---|---|---|---|---|---|----|
|    |              |                  | 1 | 2 | 3 | 4 | 5 | 6 | 7 | 8 | 9 | 10 |
| 74 | Bacterial trehalose synthase 6P | Tre-6P | | | + | | | | | | | + |
| 75 | Bacterial multidrug efflux pump AB | acfAB | | + | | | | | | | | + |
| 76 | Bacterial Sigma S factor | RpoS | | | | | | | | | | + |
| 77 | Bacterial Sigma-B factor | Sigma-B | | | | | | | | | | + |
| 78 | Bacterial DNA-binding protein stationary phase | dps | | | | | | | | | | + |
| 79 | Bacterial GroE | GroE | | | + | | | | | | | + |
| 80 | Bacterial DnaK-DnaJ | DnaK-DnaJ | | | + | | | | | | | + |
| 81 | Bacterial GroES-GroEL | GroES-GroEL | | | + | | | | | | | + |
| 82 | Catalase | Cat | + | | | | | | | | | |
| 83 | Hypoxia induced factor 1alpha | HIF-1 | + | | | | | | | | | |
| 84 | Glutathion peroxidase | GSHPx | | + | | | | | | | | |
| 85 | Carbonic anhydrase | CAA | + | | | | | | | + | | |
| 86 | Ornithine decarboxylase | ORD | + | | | | | | | | | |
| 87 | Vasoendothelial growth factor | VEGF | + | | | | | + | | | | |
| 88 | Erythropoietin | EPO | + | | | | + | + | | | | |
| 89 | Melatonin | Melatonin | | | | | | + | | + | | |
| 90 | Thyroid-stimulating hormone receptor | TSHR | | | | | | + | | | | |
| 91 | Methenyl-tetrahydro-folate reductase | MTHFR | | | | | | + | | | | |
| 92 | Nucleostemin | Nucleostemin | | | | | + | + | | | | |
| 93 | OCT-4 | OCT-4 | | | | | | + | | | | |
| 94 | Salivary alpha-amylase | SAA | | | | | | | | + | | |
| 95 | Norepinephrine | Norepinephrine | | | | | | | | + | | |
| 96 | Epinephrine | Epinephrine | | | | | | | | + | | |
| 97 | Oxytocin | Oxytocin | | | | | | | | + | | |
| 98 | Thromboxane synthase1 | TBXAS1 | | + | | | | + | | | + | |
| 99 | C-reactive protein | C-reactive protein | | | | | | | | | + | |
| 60 | TNF-alpha | TNF | | | | | | | | | + | |
| 61 | Apolipoproteins A and B | apoB, apoC | | + | | | | + | | + | + | |

FIGURE 4
Two-Tier SR Biomarker Assay
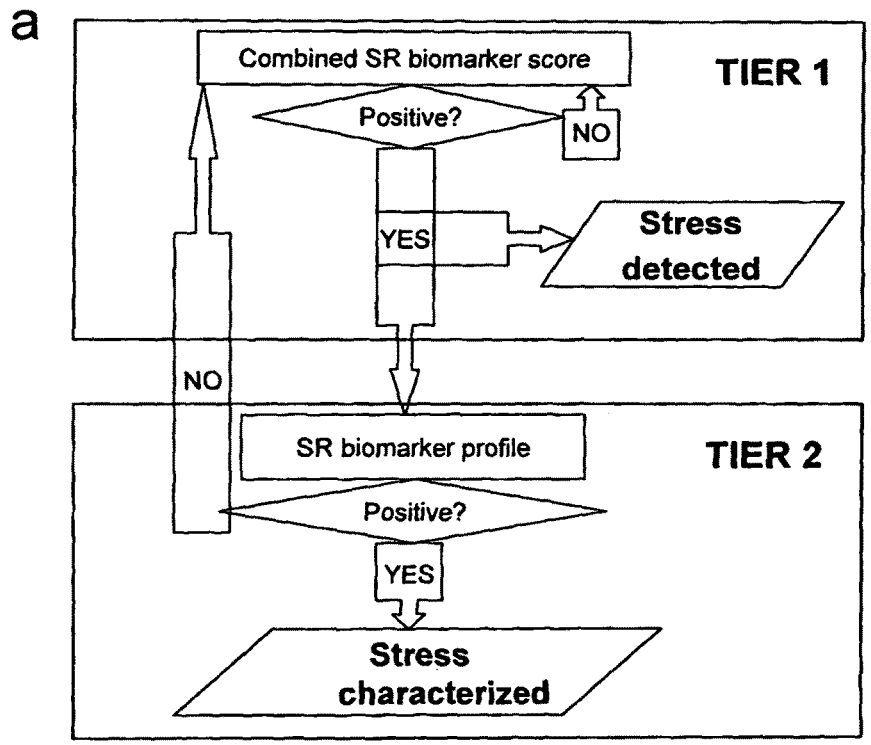
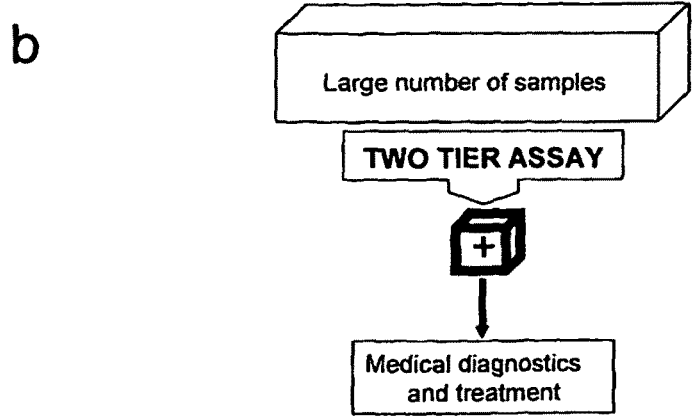

FIGURE 5

Antibodies for immunochemical assays of SR biomarkers

| SR biomarker | Antibodies specific for SR biomarkers | | | | |
|---|---|---|---|---|---|
| | Host | Format | Optimal dilution | | Cross-reactivity |
| | | | Single antibody | Antibody pool[a] | Antibody pool[b] | |
| Endorphin | R | Whole serum | 1:2,000 | 1:80,000 | 1:75,000 | H, W, U, C, R, P, A, F, I, L |
| Caspase 8 | R | Whole serum | 1:4,000 | 1:160,000 | 1:270,000 | H, U, C, R, B, A, F,I, L |
| Cyclin D | M | 1.0 mg/ml | 1:600 | 1:24,000 | 1:36,000 | H, U, C, R, B, A, F |
| Cox-2 | R | 0.2mg/ml | 1:300 | 1:12,000 | 1:18,000 | H, U, R, B, F |
| CYP450 | R | Whole serum | 1:2,000 | 1:80,000 | 1:150,000 | H, W, U, C, R, B, A, F, I, T |
| Cyt c | M | 0.775 mg/ml | 1:1,500 | 1:60,000 | 1:27,000 | H, U, R, B, A, I |
| EGFR | R | Whole serum | 1:400 | 1:16,000 | 1:18,000 | H,U, C, R, A, F, I, L |
| Ferritin | R | 2.3mg/ml | 1:2,000 | 1:80,000 | 1:18,000 | H, U, C, R, B, A, F, T |
| GR | R | 0.2mg/ml | 1:1,500 | 1:60,000 | 1:36,000 | H, U, C, R, B, A, F |
| Grp58 | R | Whole serum | 1:1,000 | 1:40,000 | 1:60,000 | H, U, C, R, F |
| Grp75 | M | Ascites | 1:800 | 1:32,000 | 1:36,000 | H, U, C, R, F, I |
| GST | R | 1.03mg/ml | 1:400 | 1:16,000 | 1:27,000 | H, U, R, B, F, I |
| Hsp25 & Hsp27 | R & M | Whole serum & 0.8 mg/ml | 1:2,000 &1:150 | 1:80,000 & 1:6,000 | 1:60,000 & 1:5,000 | H, U, C, R, B, I, L |
| Hsp40 | R | Whole serum | 1:6,000 | 1:240,000 | 1:240,000 | H, W, U, R, B, A, F, I |
| Hsp60 | R | Whole serum | 1:1,000 | 1:40,000 | 1:75,000 | H, W, R, B, F, I, L, T |
| Hsp90 | M | 1.0 mg/ml | 1:600 | 1:24,000 | 1:24,000 | H, W, U, C, R, B, A, F, I, L |
| HSF-1 | R | Whole serum | 1:2,000 | 1:80,000 | 1:120,000 | H, U, C, R, B, A, I |
| HO-1 | R | Whole serum | 1:1,500 | 1:60,000 | 1:48,000 | H, U, C, R, B |
| IL-1 | R | 0.2mg/ml | 1:500 | 1:20,000 | 1:27,000 | H, W, U, C, R, B, P, F, I |
| IL-6 | R | 0.2mg/ml | 1:800 | 1:32,000 | 1:27,000 | H, W, U, C, C, R, I, L |
| IL-8 | R | 0.2mg/ml | 1:600 | 1:24,000 | 1:27,000 | H, U, C, R, F, I |
| IL-10 | R | 0.2mg/ml | 1:300 | 1:12,000 | 1:18,000 | H, U, R, M, F |
| IL-12 | R | 0.2mg/ml | 1:300 | 1:12,000 | 1:27,000 | H, U, C, R, M, F |
| Laminin | R | Whole serum | 1:25 | 1:1,000 | 1:1,500 | H, W, U, C, R, B, A, F, I |
| Leptin R | M | 0.2mg/ml | 1:5 | 1:200 | 1:600 | H, W, U, R, B, A, F |
| MT | M | 0.1mg/ml | 1:4,000 | 1:160,000 | 1:36,000 | H, W,U, C, R, F, I |
| Mekk-1 | R | 1.0 mg/ml | 1:500 | 1:20,000 | 1:36,000 | H, R, F |
| Mek-1 | R | 1.0 mg/ml | 1:500 | 1:20,000 | 1:36,000 | H, U, R, A, I |
| CYP red | R | Whole serum | 1:1,000 | 1:40,000 | 1:48,000 | H, U, R, A, L |
| iNOS | R | 0.5mg/ml | 1:300 | 1:12,000 | 1:18,000 | H, U, R, A, F, I, L |
| Fos | R | 10-20mg/ml | 1:300 | 1:12,000 | 1:18,000 | H, U, C, R, B, A, F, I |
| Jun | R | 10mg/ml | 1:25 | 1: 1,000 | 1:1,500 | H, U, R, A, F, I, L |
| Serotonin R | R | 0.2mg/ml | 1:400 | 1: 16,000 | 1:18,000 | H, U, C, R, B, F, I, L |
| Serotonin | R | Whole serum | 1:150 | 1: 6,000 | 1:9,000 | |
| Substance P | R | Whole serum | 1:300 | 1:12,000 | 1:27,000 | H, W, U, R, B, A, I |
| SOD Mn | R | 1.52mg/ml | 1:3000 | 1:120,000 | 1:120,000 | H, U, C, R, B, A, F,I, L |
| SOD Cu/Zn | R | 1.0 mg/ml | 1:5,000 | 1:200,000 | 1:75,000 | |
| TGF | R | 0.2mg/ml | 1:500 | 1:20,000 | 1:24,000 | H, U, C, R, B, F |
| p53 | M | 0.5mg/ml | 1:800 | 1:32,000 | 1:36,000 | H, W, U, R, B, A, F, I, L |
| VIP | R | Whole serum | 1:1,000 | 1:40,000 | 1:120,000 | H, W, U, R, B, P, F, I |

Single antibodies were used individual SR biomarker assays
[a] Pooled antibodies for combined SR biomarker assay in all samples
[b] Pooled antibodies for combined SR biomarker assay in spotted dolphin samples SR Biomarker Profiles in Reference Skin Samples SR Pathway Profiles in Reference Skin Samples Combined SR Biomarker Scores in Prostate Cancer

SYSTEMS AND METHODS FOR ANALYZING PERSISTENT HOMEOSTATIC PERTURBATIONS

CROSS REFERENCE TO RELATED APPLICATIONS

This application is a 35 USC §371 National Stage application of International Application No. PCT/US2008/004448 filed Apr. 4, 2008, now pending; which claims the benefit under 35 USC §119(e) to U.S. Application Ser. No. 60/910,158 filed Apr. 4, 2007, now abandoned. The disclosure of each of the prior applications is considered part of and is incorporated by reference in the disclosure of this application.

FIELD OF THE INVENTION

This invention is in the field of homeostasis analysis. More particularly, it relates to systems and methods for analyzing persistent homeostasis perturbations, i.e., chronic stress, by measuring levels of biomarkers that are related to chronic stress. This invention is also directed to systems and methods for analyzing the molecular mechanisms of chronic stress.

BACKGROUND OF THE INVENTION

The health of living organisms is maintained through a self-regulatory process called homeostasis. Limited, short-term perturbations of homeostasis caused by routine hardships do not affect health. In contrast, persistent long-term perturbations of homeostasis, also called "chronic stress," are often associated with health disorders. Conditions that cause stress are called "stressors."

Stress is a systemic condition and can therefore be analyzed not only in cells that were originally impacted by a stressor, but can also be analyzed in remote cells, tissues and biofluids. This is because stress triggers the activation of adaptive stress responses via a network of stress response (SR) pathways whose function is the maintenance of homeostasis. This network is large and involves hundreds of pathways and molecules. Varied groups of the SR pathways are activated by different stressors, in different organisms, and in different sample types. However, a small subset of the SR pathways respond universally to stress. These "universal" SR pathways are reproducibly activated by most stressors in most organisms.

Stress affects people at all ages. In addition to humans, stress also affects all living organisms (e.g. animals, plants and microorganisms) as well as entire ecosystems consisting of multiple different organisms. Stress has been linked to the risk and severity of health disorders and diseases. Stress also has adverse effects on reproduction, on the aging process and on longevity.

Current laboratory tests for stress rely on the measurement of hormones such as glucocorticoids (e.g. cortisol) and catecholamines (e.g. norepinephrine) in blood and saliva. (Arch. Gen. Psychiatry, 61: 394-401 (2004); Blood Pressure, 13: 287-294 (2004); and International Journal of Hygiene and Environmental Health, 208: 227-230. (2005).) These hormones are not suitable targets for a general analysis of stress, because they are not relevant to many types of stressors. Moreover, these individual stress biomarkers alone cannot discriminate between stress and responses to short-term hardships, such as school exams or exercise. Furthermore, these hormone-based stress tests are not useful to analyze the molecular mechanism of stress because these two biomarkers are only related to two SR pathways; the limbic hypothalamic-pituitary-adrenal axis (glucorticoids) and the sympathetic nervous system (catecholamines.) These two pathways are not representative of the universal SR pathways associated with chronic stress brought on by a broad range of different stressors. Indeed, many types of stressors do not activate these pathways. For example, these pathways are not activated by toxic chemicals. Moreover, these two stress tests have very limited applications in veterinary care, wildlife conservation and ecology, because they are not suitable for most nonhuman species.

There is therefore a need for systems and methods that are useful to analyze persistent homeostatic perturbations (i.e. chronic stress) caused by diverse types of stressors in many different types of organisms. There is also a need for methods that are useful to analyze the molecular mechanism of chronic stress in order to guide the development of new tools for diagnostics, prevention and treatment of stress.

SUMMARY OF THE INVENTION

The present invention provides systems and methods for analyzing persistent homeostatic perturbations by measuring levels of biomarkers that are related to chronic stress.

In one embodiment, the invention is a method of analyzing persistent homeostatic perturbations in a sample from a given source suspected of being exposed to a stressor, comprising the steps of: constructing a panel of at least three stress response (SR) biomarkers, wherein the stress response biomarkers are selected for the panel based on their known or suspected association with at least two SR pathways; measuring the SR biomarker levels in the sample; and converting the SR biomarker level measurements into a SR biomarker profile to analyze the homeostatic perturbations.

The samples that are useful in the practice of the present invention can be take any form, such as solid, fluid or gas, and can come from a variety of different biological or nonbiological sources such as whole blood, blood serum, blood plasma, saliva, exhaled breath, urine, cerebrospinal fluid, fluid derived from a tissue, bone marrow, lavage fluid, cell culture fluid, fluid derived from an organ, lymphatic fluid, tears, sweat, seminal fluid and vaginal fluid. The organ-specific tissue may be, for example, skin, prostate tissue, or breast tissue.

The persistent homeostatic perturbations analyzed by performing the method of the present invention may be caused by a stressor associated with a physical condition, a biological condition, a psycho-social condition or a chemical agent.

The stress response (SR) biomarkers that are the targets of the systems and methods of the present invention may be previously known to be or suspected of being associated with SR pathways, such as: β-endorphin, caspase 8, cyclin D1, cyclooxygenase 2, cytochrome P450, cytoplasmic cytochrome C, epidermal growth factor receptor, ferritin, glucocorticoid receptor, glucose regulated protein Grp58, glucose regulated protein Grp75, glutathione S-transferase π, heat shock protein 25/27, heat shock protein 40, heat shock protein 60, heat shock protein 70, heat shock protein 90, heat shock transcription factor HSF-1, heme oxygenase-1, interleukin IL-1β, interleukin IL-6, interleukin IL-8, interleukin IL-10, interleukin IL-12, laminin, leptin receptor, metallothionein, stress-activated MAP kinase Mekk-1, mitogen-activated MAP kinase Mek-1, NADPH-cytochrome P450 reductase, inducible nitric oxide synthase II, proto-oncogene c-Fos protein, proto-oncogene c-Jun protein, serotonin receptor, serotonin, substance P, superoxide dismutase Mn, superoxide dismutase Can, transforming growth factor β, tumor suppressor p53 and vasoactive intestinal peptide.

Other SR biomarkers are listed in FIG. 3, or can easily be identified from a review of the scientific literature.

A SR biomarker panel may comprise or consist of all of the aforementioned SR biomarkers listed in FIG. 2, or FIGS. 2 and 3.

As indicated in FIG. 2, the listed SR biomarkers are known to be associated with the following SR pathways; redox, xenobiotics, chaperoning, cell growth, cell death, adhesion, neuroendocrine signaling, immunity, deoxyribonucleic acid repair and microbial activation.

An important aspect of the present invention is the recognition that chaperoning as a SR pathway is uniquely associated with numerous different stressors in a variety of samples from a variety of organisms. Accordingly, constructing a panel of SR biomarkers known to be associated with chaperoning can provide useful information about persistent homeostatic perturbations without including SR biomarkers associated with any other SR pathways. Thus, in one embodiment, the SR biomarkers in the panel are selected from: glucose regulated protein GRP58, glucose regulated protein GRP75, heat shock protein 25/27, shock protein 40, heat shock protein 60, heat shock protein 70, heat shock protein 90 and interleukin IL-6.

One representative SR biomarker panel includes at a minimum the following SR biomarkers: heat shock transcription factor HSF-1, super oxide dismutase Cu, stress activated mitogen activated protein kinase Mekk-1, super oxide dismutase Mn and ferritin.

In an alternative embodiment, SR biomarkers are selected for inclusion in the SR biomarker panel that are known to be associated with redox control, chaperoning or microbial activation.

The type of assay (i.e., assay format) that is useful in the practice of the present invention can be based on any assay known to be useful to measure nucleic acid, protein or small molecule biomarkers. For example, when the SR biomarker is a protein, the assay can be performed by conducting immunohistochemical staining, flow cytometry, enzyme linked immusorbant assays, or immunoprecipitation assays.

In one embodiment, the measured levels of SR biomarkers are converted into a normalized and log-transformed SR biomarker score for more convenient data processing.

Another important aspect of the invention is that the SR biomarker score is useful in constructing a SR biomarker profile that has characteristics reflective of the type of sample, the source of the sample and the nature of the stressor. Such SR biomarker profiles are ideally capable of classifying the sample as coming from a normal subject or a subject exposed to the stressor.

In addition to SR biomarker profiles, the SR biomarker measurements can be used to construct a SR pathway profile, the characteristics of which reflect the nature and degree to which individual SR pathways are activated as a response to certain stressors.

The source of the sample may be an organism from a taxonomic grouping of organisms selected from the group consisting of: vertebrate animals; invertebrate animals; protists and fungi; bacteria; and plants.

In an alternative embodiment, the method of the present invention is a method for constructing a panel of stress response (SR) biomarkers for analyzing persistent homeostatic perturbations in a test sample from a given source suspected of being exposed to a stressor, comprising the steps of: obtaining reference samples from the same source, some of which are normal and some of which have been exposed to the stressor; identifying candidate SR biomarkers for the panel based on their known or suspected association with SR pathways; measuring the candidate SR biomarker levels in the reference samples; and selecting the candidate SR biomarkers for inclusion in the panel, wherein the panel includes a sufficient number of the candidate SR biomarkers to differentiate between the normal samples and the samples exposed to the stressor to a preselected reliability level.

The preselected reliability level may be 100%, in which case the SR panel can distinguish all normal samples from all abnormal samples (i.e., those from subjects exposed to the stressor), or it can be less than 100% reliable, such as 90% or 75% reliable. It is not necessary for the methods of the present invention to provide for an absolute differentiation between normal and abnormal samples, since the SR biomarker profiles and SR pathway profiles provide a pattern of data that is useful in analyzing the stress response, regardless of the lack of absolute differentiation.

The SR biomarker panel thus constructed may include the same biomarkers described above and/or different SR biomarkers known to be or suspected of being associated with chronic stress.

Using the SR biomarker panel of 40 preferred biomarkers, panels with less than all 40, and in some cases as few as 3, can be constructed and still be quite useful for analyzing persistent homeostatic perturbations by generating SR biomarker profiles and or SR pathway profiles therefrom.

One alternative embodiment of the present invention is to measure SR biomarker level decreases, rather than increases, as a way of monitoring stress interventions such as a disease treatment protocol. Example 9 describes just such a method involving massage as an intervention for stress, and the results described therein show how the SR biomarker score decreases as a result of such intervention.

Other aspects of the invention are described throughout the specification. Accordingly, these and other features, aspects, and advantages of the present invention will become better understood with reference to the following description, appended claims, and accompanying drawings.

BRIEF DESCRIPTION OF THE DRAWINGS

FIG. 2 is a table describing a panel of 40 SR biomarkers and their associations with SR pathways. The pathways referenced in the Figure are: 1—redox control, 2—cellular detoxification Phase I and II, 3—chaperoning, 4—DNA repair, 5—cellular adhesion and motility, 6—cell cycle and growth, 7—cell death, 8—neuro-endocrine signaling, 9—immunity, 10—microbial activation. The Figure also shows the different taxonomic groups of organisms that the SR biomarkers are expressed in. The taxonomic groups referenced in the Figure are: 1—vertebrate animals, 2—invertebrate animals, 3—protists and fungi, 4—bacteria; 5—plants. (*) Biomarkers expressed in all taxonomic groups.

FIG. 3 is a table listing of additional SR biomarkers.

FIG. 4 depicts a two-tier SR biomarker assay. In FIG. 4a, a flow chart for detecting and characterizing stress is depicted. Tier 1 uses combined SR biomarker scores to provide a low resolution test suitable for a general detection of stress. Tier 2 uses SR biomarker profiles to provide a high resolution test suitable for classification and characterization of the stress identified by Tier 1. FIG. 4b depicts the use of the two-tier SR biomarker assay for screening of a large sample set and selecting samples with critical stress levels (+) for medical diagnostics and treatments.

FIG. 5 is a table listing antibodies specific for 40 SR biomarkers, along with their optimized concentrations for the use in individual or combined SR biomarker assays. The antibodies are useful in the practice of the present invention. Immunological cross-reactivity of the antibodies is as follows: H, human; W, whales and dolphins; U, ungulates (cow, goat, sheep, pig, horse); C, carnivores (cat, dog, seal); P, reptiles (snake, turtle); R, rodents (rabbit, guinea pig, rat, mouse); M, marsupials (kangaroo); B, birds (chicken, duck, sparrow); A, amphibians (frog); F, fish; I, invertebrates (insects, worms, spiders, sea urchins, jelly fish, lobsters, clams, hydra); L, lower eukaryotes (fungi, protists, algae, molds). T, bacteria.

In FIG. 8a, profiles based on the 40 SR biomarker panel are depicted. FIG. 8b depicts profiles based on a 5 SR biomarker panel. Both SR biomarker panels distinguished control and stressed samples (clusters A and B) with 100% reliability.

DETAILED DESCRIPTION OF THE INVENTION

The present invention relates to systems and methods for analyzing persistent homeostatic perturbations, i.e. chronic stress, by measuring levels of biomarkers that are related to chronic stress. This invention is also directed to systems and methods for analyzing the molecular mechanisms of chronic stress, and to methods for screening potential therapeutic interventions for their effects on chronic stress.

Biological responses to stressors involve hundreds of highly integrated molecular pathways. However, to practically analyze chronic stress, a small number of "universal pathways" have been identified that reproducibly respond to most stressors in most organisms, and in particular, essentially all vertebrates. Functional activation of these universal pathways by stressors generates reproducible patterns of data that can be monitored to analyze the characteristics and effects of chronic stress.

The methods described herein are referred to as "stress response profiling" or "SR profiling," because they relate to the measurement of the levels of multiple SR biomarkers by performing SR biomarker assays, where the SR biomarkers are associated with multiple stress response pathways that are reproducibly activated by chronic stress (i.e., the universal SR pathways.) The results of such multi-dimensional SR biomarker assays can be used to construct a "profile" (i.e. a pattern of data, which is also referred to in the industry as a "signature" or a "fingerprint") that is characteristic of the type of stress, the organism and/or the sample type.

Figure 1:
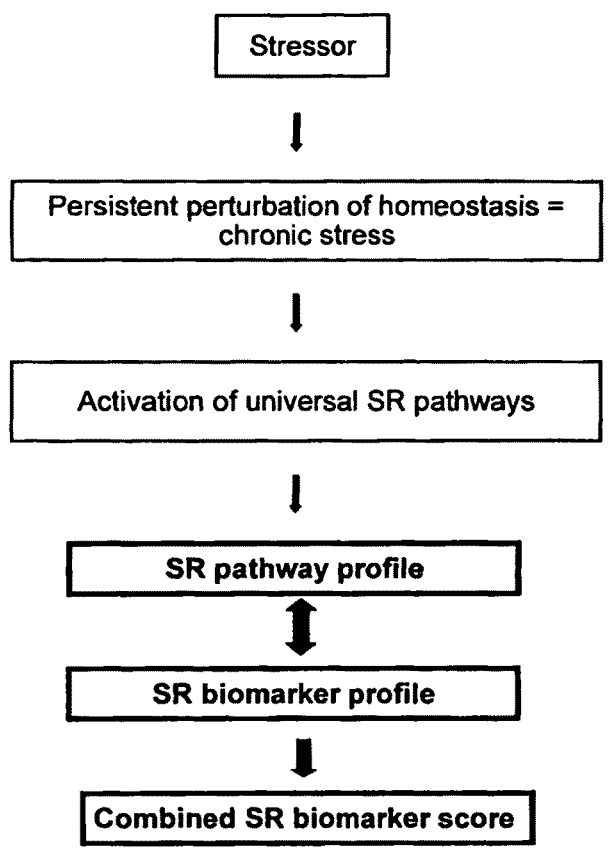
FIG. 1 is a flow chart describing the relationship between stressors, SR pathways and SR biomarkers.

As depicted in FIG. 1, stressors can trigger persistent perturbations of homeostasis, i.e., they cause chronic stress. Biological responses to chronic stress (also referred to as "adaptive stress responses") can be categorized in terms of the SR pathways they activate, which are further characterized in terms of the SR biomarkers associated with these pathways. Thus, SR profiling of either or both the SR pathway activation or the SR biomarker levels resulting from such activation can be utilized to provide molecular signatures of biological responses to stressors that threaten health, such as stressors that cause chronic stress. Such SR profiling is therefore useful, in part, to predict increased risk of disease.

DEFINITIONS

Unless defined otherwise, all technical and scientific terms used herein have the same meaning as is commonly understood by one of skill in the art to which this invention belongs.

As used herein, the term "living organism" or simply "organism" is to be understood as encompassing all biological forms that are single cells or multicellular bodies.

As used herein, the term "homeostasis" is a biological process that maintains the health of organisms.

As used herein, the term "persistent homeostatic perturbation" is to be understood as a homeostatic change that has an adverse affect on the health of organisms. It is another way of referring to "chronic stress" or simply "stressed" which should be understood to mean a persistent perturbation of homeostasis and encompassing all forms of chronic cellular stress and chronic physiological stress.

As used herein, the term "stressor" is to be understood as all forms of agents or conditions that give rise to stress. Stressors according to the present invention include agents and conditions that are in the outer environment of organisms such as the air temperature as well as agents and conditions that are in the inner environment of organisms such as a disease.

As used herein, the term "adaptive stress response" or simply "stress response" is to be understood as a homeostatic process that provides a countermeasure to stress.

As used herein, the term "stress response pathway" is to be understood as the form of the stress response that has a specific function in the organism, such as DNA repair. Stress response pathways are embodied in expressed molecules (i.e., SR biomarkers.)

As used herein, the term "universal stress response pathway" or simply "SR pathway" is to be understood as a form of stress response to most stressors, in most organisms. Functional activation of these SR pathways generates reproducible patterns of expressed molecules.

As used herein, the term "SR biomarker" is to be understood as an expressed molecule known to be or suspected of being associated with activation of a SR pathway.

As used herein, the term "SR biomarker profile" is a multi-dimensional pattern of data whose components are at least two SR biomarker scores for individual SR biomarkers across a SR biomarker panel.

As used herein, the term "SR pathway profile" is a multi-dimensional pattern of data representing at least two SR pathways. The components are functions of SR biomarker scores related to the individual SR pathways. The functions yield one-dimensional data points that provide simple-to-use indices of activation levels for the individual pathways.

As used herein, the term "stress response profiling" refers to constructing either or both SR pathway profiles or SR biomarker profiles from SR biomarker assays.

As used herein, the term "SR biomarker panel" is to be understood as at least two SR biomarkers that as a group provide enhanced information about stress responses than single SR biomarkers.

As used herein, the term "SR biomarker panel score" or "panel score" is to be understood as a one-dimensional data point calculated as the average of SR biomarker scores across a SR biomarker panel.

As used herein, the term "SR biomarker score" is to be understood as a normalized and optionally log-transformed measurement of a SR biomarker.

As used herein, the term "measurement" of a SR biomarker is to be understood as a quantitative or qualitative determination of the SR biomarker's expression level in a sample from an organism.

As used herein, the term "individual SR biomarker assay" or "SR biomarker assay" is to be understood as an assay of individual SR biomarkers.

As used herein, the term "combined SR biomarker assay" is to be understood as an assay that yields measurements representative of the combined expression levels for a panel of SR biomarkers.

Stressors

Stress can be caused by a variety of sources of stressful conditions, i.e. "stressors." These stressors can be agents or conditions whose nature is physical, chemical, biological and/or psycho-social. Stressors are present in the external environment, for example air temperature, and also in the internal environment of a biological system, for example genetic defects, obesity or chronic diseases. Most real world stressors are complex mixtures of agents and conditions. For example, a military combat operation in a tropical mountain terrain is a complex stressor that might involve adverse effects of heat, altitude, humidity, noise, pesticides, drugs against warfare agents drugs, insect bites, strenuous exercise, sleep deprivation and conditioned fear.

Some stressors affect all organisms, for example, heat and radiation, while other stressors affect only one or a few types of organisms, for example the HIV virus affects only humans and several primates.

In humans, representative stressors are shown in Table 1 below:

TABLE 1

Representative Stressors in Humans

| Physical | Chemical | Biological | Psycho-social |
|---|---|---|---|
| heat, cold, light (uv, X-ray), radioactivity, pressure (osmotic, mechanical), noise, altitude, gravity | natural and industrial toxic chemicals including heavy metals, polycyclic and halogenated hydrocarbons, petroleum, pesticides, warfare agents, carbon monoxide, ozon, drugs, alcohol, tobacco smoke, abnormal oxygen concentration (hypoxia), abnormal salt concentration (hyponatremia), dehydration, starvation. | disease-causing microorganisms, genetic defects, chronic diseases, injury, surgery, obesity, hypertension, sleep deprivation, strenuous exercise. | psychological trauma, restraint, out-of-control harm, defeat, conditioned fear, over crowding, social disorganization, mother-child separation, parental neglect. |

Stress Response Pathways

Even though the biological response to a stressor typically involves hundreds of molecular processes, a small subset of these molecular processes are universally activated by essentially all types of stressors, but to different degrees. Such activation generates a reproducible pattern that defines the biological response to the stressor, and can be referred to as a stress response (SR) pathway profile.

Preferred universal SR pathways, or simply "SR Pathways" are listed below in Table 2:

TABLE 2

SR Pathways

| | Pathway | Referred to as: |
|---|---|---|
| 1 | Free radical scavenging, redox homeostasis | Redox |
| 2 | Cellular detoxification Phase I, II; xenobiotic removal. | Xenobiotics |
| 3 | Chaperoning, protein folding | Chaperoning |
| 4 | DNA repair | DNA repair |
| 5 | Cellular adhesion | Cell adhesion |
| 6 | Regulation of cellular cycle and growth | Cell growth |
| 7 | Regulation of cellular death, apoptosis, necrosis | Cell death |
| 8 | Neuroendocrine signaling | NE signaling |
| 9 | Regulation of innate and specific immunity | Immunity |
| 10 | Microbial activation | Microbial activation |

SR pathway profiles can be based on activation of all ten pathways listed in Table 2, or they may be based only on SR pathways 1 to 9 or 1 to 8.

Although all of the aforementioned SR pathways are well characterized and described in the literature; the following brief descriptions are included to facilitate understanding of their molecular nature:

Redox control (1). This pathway regulates levels of reactive oxygen and nitrogen species (superoxide, nitric oxide, carbon monoxide) through free radical scavenging proteins such as superoxide dismutases. Free radicals are essential cellular mediators but when in excess, they cause cellular dysfunction through damaging lipids, proteins, DNA and membrane integrity.

Cellular detoxification (2). Cellular detoxification provides a defense against chemical threats to cellular integrity. Phase I detoxification is a cytochrome P450 driven process for metabolizing a wide variety of endogenous metabolites (e.g. fatty acids, steroids) and foreign substances (drugs, alcohol, pesticides and hydrocarbons). Phase II is based on the glutathione metabolism and provides cellular resistance to oxidants, hydrocarbons and heavy metals.

Chaperoning (3). Chaperones fold newly synthesized polypeptides and denatured proteins and for prevent uncontrolled protein aggregation. Chaperoning involves hundreds of "client" proteins and therefore has a key role in multiple biological functions including cellular protection, metabolism, growth, the development of multicellular organisms and molecular evolution. Excessive chaperoning facilitates disease by folding "wrong" clients such as the diphtheria toxin or mutant p53 that are cytotoxic or cause cancer.

DNA repair (4). DNA damage is ubiquitous and therefore the stability of the genome is under a continuous surveillance by multiple DNA repair mechanisms. DNA lesions are produced during transcription and replication, and by metabolic and immunity by-products (e.g. free radicals produced during aerobic respiration and by immune cells killing bacteria). DNA can be also damaged by environmental mutagens such as oxidants, heavy metals, radiation and viruses. The DNA repair pathway regulates multiple stages and mechanisms of DNA repair, and is closely linked with cell cycle control and apoptosis.

Cellular adhesion and motility (51. This pathway monitors cellular interactions with the extracellular matrix and also changes in cytoskeletal matrix such as centrioles, kinetosomes and other microtubule organizing centers. These processes are essential for cellular survival, growth, metabolism and motility, and also for the formation of microbial biofilms and microbial-host interactions.

Cell growth (6). In multicellular organisms, cell cycle progression is strongly regulated during the development and modulated by growth factors (mitogens), disease and environmental stress. In mature tissues, most cells do not divide. Cycling cells in tissues are typically somatic stem cells involved in normal tissue turnover (e.g the germinal layer of the skin). Cell cycling is typically arrested in starved cells and in cells with DNA or mitochondrial damage. Increased cell growth occurs during immune responses, wound healing and regeneration of tissues damaged by environmental stress, toxins, disease or infection. Uncontrolled, excessive cell growth is found in cancer.

Cell death (7). The programmed cell death (apoptosis) "recycles" cellular components and prevents the release of toxins from dying cells, as happens during necrotic cell death. In animal tissues, apoptosis is increased in areas of tissue remodeling and wound healing, and during aging. During a disease, apoptosis can be increased within the diseased tissue (e.g. psoriatic skin lesions) and/or in remote tissues and biofluids (e.g. HIV Tat protein is a soluble mediator that triggers apoptosis in uninfected lymphocytes). Apoptosis can be also triggered by environmental stressors that cause mitochondrial damage (e.g. oxidative stress and uv light).

Neuro-endocrine signaling (8). This pathway is crucial for regulating physiological homeostasis and behavioral regulation in animals including simple invertebrates. It involves a large number of mediators (hormones, neuropeptides, neurotransmitters) and cellular receptors produced by specialized tissues (glands and neural tissues), and also locally in peripheral tissues (e.g. skin and gut). In vertebrates, two signaling mechanisms provide initial responses to stress: the limbic hypothalamic-pituitary-adrenal (LHPA) axis that involves glucocorticoids (e.g. cortisol) and the sympathetic nervous system activation via catecholamines. However, chronic stress also activates signaling of pain and anxiety, energy balance, metabolism, respiration, circulation and reproduction. Neuro-endocrine and immune signaling are integrated through common mediators and provide coordinated responses to environmental stress and disease.

Immunity (9). Immunity provides a systemic defense against biological threats to organism's integrity such as injuries, tumors and disease-causing microorganisms. Innate immunity provides a nonspecific defense through soluble mediators (e.g. chemokines, agglutinins) and specialized cells (e.g. macrophages) that circulate through the organism and inactivate parasitic microorganisms, engulf apoptotic cell debris and kill infected and tumor cells. Innate immunity is found in protists, animals and plants. Vertebrates use innate immunity during the initial phases of stress response because it takes several days to activate specific immunity that provides threat-specific antibodies and lymphoid cells. Immune regulation is mediated through numerous signaling proteins called cytokines or interleukins. Increased immunity can be beneficial (e.g. short-term immune activation that removes a bacterial infection) or harmful (e.g. chronic inflammation and autoimmunity increase physiological stress through oxidative stress and apoptosis).

Microbial activation (10). This pathway monitors the activation of stress responses in microorganisms (bacteria, fungi, viruses), and signaling between microorganisms and host cells. Commensal microbial biofilms are an integral part of animal and plant bodies and contribute to physiological homeostasis. In animals, microbial biofilms are primarily associated with the inner and the outer body surfaces (the mucosal epithelium and the skin). Therefore microbial biofilms are sensitive both to environmental stressors (e.g. uv light) as well as to micro-environmental conditions in host tissues and body fluids (e.g. oxidative stress). During physiological stress, increased signaling between microbial biofilms and host cells promotes protection of the organism through modulating host's stress responses. For example, signaling by gastrointestinal microflora modulates levels of proteins with key roles in redox control, cellular detoxification, chaperoning, cell growth, apoptosis and immunity such as metallothionein, Hsp25, ferritin, p53, TGF beta, IL-8 and IL-10. When pathogenic microorganisms invade animals or plants, their stress responses are elevated, which in turn increases stress responses in the host (bacterial heat shock proteins are animal superantigens). Disease-causing microorganisms also release soluble mediators that trigger cellular stress and activate multiple stress response pathways in infected as well as remote host tissues (e.g. HIV Tat protein).

Stress Response (SR) Biomarkers

Activation of SR pathways by stressors results in a pattern of expressed molecules such as genes, proteins, metabolites and lipids, referred to herein as "SR biomarkers. Accordingly, each of these biomarkers is said to be "associated with" one or more SR pathways. Measuring the levels of these SR biomarkers provides useful information about the biological effects of stressors. Preferably, the SR biomarkers are expressed molecules such as proteins or fragments thereof, so long as the fragment is capable of being recognized in an SR biomarker assay with the same sensitivity as the entire protein.

Preferred SR biomarkers and their known associations with SR pathways are listed in FIG. 2. Additional SR Biomarkers and some but not all of their known associations with SR pathways are listed in FIG. 3.

The relationship between each individual stressor and the ten SR pathways, and thus the SR biomarkers associated therewith, may not always be known, especially since the effects of many stressors on particular SR pathways is not yet well studied. For example, the effects of bird flu virus, engineered nanoparticles, and effects of deep space and deep sea or other extreme environments on each individual SR pathway may not be completely elucidated.

However, most SR biomarkers associated with the 10 SR pathways are useful targets in assays to analyze the effects of both known and unknown stressors, such as environmental stressors and/or diseases-related stressors. Accordingly, SR biomarkers associated with SR pathways are suitable targets for studying the effects of unknown stressors because they provide a response-oriented detection strategy that does not require prior knowledge of the stressor.

SR Biomarkers associated with the SR pathways are also suitable targets in studying the effects of complex stressors, some of which may be known and others of which may be unknown. These complex, or "combined" stressors, are common in real-life scenarios, and may include multiple known and unknown adverse conditions. Global warming, ozone holes, human effects on wildlife, urban pollution, natural and industrial disasters, poverty and war are examples of complex, combined stressors.

Expression of SR Biomarkers

As shown in FIG. 2, many SR biomarkers are expressed in different types of organisms. Particularly preferred SR biomarkers are expressed in all five different types of organisms as shown in FIG. 2: vertebrate animals (1); invertebrate animals (2); protists and fungi (3); bacteria (4); and plants (5).

In one example, SR biomarkers that are highly conserved in protists and fungi as well as bacteria can be assayed to analyze stress responses in all three different types of microorganisms. By targeting highly conserved biomarkers (or fragments thereof that are highly conserved), assays can be developed that are useful to perform SR profiling of different sample types from different organisms exposed to different stressors using the same reagents.

Selection of SR Biomarkers

Optimal criteria for the selection of SR biomarkers are described below:

(1) The biomarker has a functional role in SR biomarker pathways associated with stress. This criteria assures that the biomarker has a physiological association with a stress response.

(2) The biomarker has a near-constant level in healthy as well as in acutely stressed biological systems. This criteria identifies biomarkers with a stable baseline that have low variability in the absence of stress.

(3) The biomarker level is significantly modulated in at least some chronically stressed biological systems. This criteria identifies biomarkers with highly variable levels in stress.

(4) The biomarker is significantly modulated by different types of stressors. This criteria identifies biomarkers with a broad range of stress sensitivity.

(5) The biomarker level preferentially increases rather than decreases in chronically stressed biological systems. This criteria identifies biomarkers that can be combined to provide a global (cumulative) biomarker level that is elevated in stress. Global biomarker levels may be more stress-sensitive and easier to measure than individual levels for multiple biomarkers.

(6) The biomarker is present in a plurality of biological systems (e.g., ecosystems, species, cell types, tissues, bodily fluids and secretions.) This criteria identifies biomarkers with a broad range of applicability.

(7) The biomarker's structure and function have been strongly conserved during biological evolution. This criteria identifies biomarkers with a universal utility as targets from multiple biological systems so that the biomarkers can be detected using the same biomarker-recognition method, e.g. a cross-reactive antibody.

(8) The biomarker can be measured in minimally invasive samples from biological systems that can be simply collected and processed, e.g. without gloves and refrigeration. This criteria identifies biomarkers that are easy to measure.

These criteria constitute a systematic method for selecting SR biomarkers that are suitable for practical analysis of stress.

In one example, candidate SR biomarkers are first selected based on their association with universal SR pathways and expression in multiple taxonomical groups of organisms. Next, SR biomarkers are selected for inclusion in a SR biomarker panel that are suitable for practical assay formats based on their expression characteristics in assay samples such as ubiquitous distribution, consistent localization, abundant cellular levels and significant differences between reference control and stressed samples. The average SR biomarker levels in the panel are converted to "scores" and SR profiles, either of the SR biomarkers or of the SR pathways to which they are associated, provide a highly reliable classification of stress.

Once a panel of SR biomarkers is evaluated based on their multi-dimensional variability (i.e., associated with multiple SR pathways in multiple organisms and in multiple sample types), a "minimal SR biomarker panel" can next be constructed by converting the SR biomarker measurement data into SR pathway signatures that reveal molecular mechanisms of stress.

As shown in FIGS. 2 and 3, there are many known SR biomarkers associated with one or more SR pathways. These and other SR biomarkers may be selected for targeting in an assay to detect homeostatic perturbations based on the criteria listed above. SR biomarkers that satisfy all the optimal criteria are considered to have "high classification power" (i.e. their ability to distinguish one source of stress from another.) Selection of biomarkers via specified criteria provides a hypothesis-driven assay design, rather than a discovery-driven assay design such as gene arrays that typically provide large data sets with low information content, which may not be useful in identifying biomarkers with high classification power.

Construction of SR Biomarker Panels

Although detection of any of the aforementioned biomarkers individually may be somewhat useful in monitoring homeostatic perturbations of a subject biological unit or organism, it is preferred to construct a panel of selected biomarkers for separate or simultaneous detection, wherein the combined results are capable of distinguishing one stressor from another, and also capable of compensating for individual "blind spots" in stress sensitivity. As used herein, "stress response profiling" refers generically to the detection of one, more than one, or a panel of SR biomarkers.

A panel should preferably satisfy the following criteria: selected biomarkers should provide for improved stressor differentiation, and should be detectable using a universal detection strategy if desired (e.g. a pool of antibodies with different specificities that reacts with all selected biomarkers in the panel under the same reaction conditions.)

For example, a panel of SR biomarkers, at least one of which is associated with each of the eight preferred or alternatively all ten SR pathways discussed above, can be selected for detection in an assay to analyze random molecular damage as a function of a reproducible increase in global stress response activity. The SR biomarker levels that are measured in the SR biomarker assay can thereafter be converted into a "profile" (i.e. a complex multi-dimensional pattern of information) associated with the SR biomarker panel, i.e. an "SR biomarker profile."

In a specific example described in more detail elsewhere herein, the data generated from an assay in which the level of all 40 of the preferred SR biomarkers in FIG. 2 is individually determined and can be manipulated to produce output in the form of a signature that is unique to the panel and useful to easily detect changes in the signature attributed to the presence of homeostatic perturbations associated with different stressors.

It is important to note that the panel of 40 biomarkers listed in FIG. 2 was developed by first performing an extensive literature review to identify a large panel of biomarkers that satisfied most if not all of the ideal criteria, and then by validating the selection based on laboratory analysis of reference samples from a broad range of biological systems (both the types and sources of samples) that were known to be either normal or chronically stressed by many different types of stressors. This complex study resulted in the compilation of a panel of 40 biomarkers that were useful to generate SR biomarker signatures from virtually any sample type (blood, saliva, skin, etc.) from any biological unit (virus, microbe, fungus, invertebrate, vertebrate, mammal, human) suffering from any type of stress (heat, cancer, infection, etc.)

More specifically, this panel and the SR biomarker assay taught herein was shown to enable stress response profiling in 11 species of mammals and birds (human, 4 species of dolphins, 3 species of whales, elephant, chicken, duck), multiple cell types (epithelial cells, fibroblasts, endothelial cells, monocytes/macrophages, lymphocytes, seminal cells, neurons, astrocytes, glial cells, microbial cells), multiple tissues (the skin, the brain, the breast, the prostate, the tonsil, the thymus) and multiple body fluids (blood, saliva, semen, breast milk).

The availability of this universal SR biomarker panel enables the validation of any newly constructed candidate panels of biomarkers that have been compiled according to the teachings herein that are more specifically tailored to particular sample types, biological units and stressors. Such candidate panels can easily be optimized against reference samples to eliminate individual SR biomarkers with insufficient variation and/or sensitivity.

It should also be apparent to anyone of skill in the art that the exemplified panel of 40 SR Biomarkers can be used to validate smaller sized panels consisting of less than all 40 SR Biomarkers. For example, an appropriate statistical method can be used to select the "best" SR Biomarkers for inclusion in a panel. For example, principal component analysis (PCA) can be used to determine variability in SR biomarker expression profiles in reference samples (i.e., known normal and known abnormal samples). The PCA data can be used to calculate a variability index.

For example, a panel can be constructed by selecting SR Biomarkers with the highest variability index values and using appropriate statistical method to determine the classification power of the panel for reference samples. For example, hierarchic clustering can be used to determine the classification power of SR biomarker panels. The classification power corresponds to the reliability with which the SR biomarker panel discriminates between the normal and the abnormal samples. In other words, the reliability shows how "good" is the SR biomarker panel in separating normal and abnormal samples. The reliability level can be selected by the end user of the panel. Accordingly, as few as two SR Biomarkers can constitute a panel and provide enough information to classify abnormal samples. Preferably, however, the panel will include at least 5 SR Biomarkers with the highest variability indices in reference samples.

Two-Tier Test

The SR biomarker assays of the present invention can also be performed in a two-tier approach. The first tier is a combined SR biomarker assay (i.e., simultaneous measurement of all SR biomarkers in a single assay system, or pooling results from individual SR biomarker measurements.) This first tier is a low-resolution test to first discriminate between samples/subjects with different levels of stress. The second tier is a high-resolution test to further characterize the stress. This type of two-tier testing approach is ideally suited for performing a quick triage of samples for rapid assessment of health disorders and other manifestations of chronic stress (Tier 1), followed by a more thorough analysis to facilitate intervention (Tier 2.) Such a test format is depicted in FIG. 4.

As shown in FIG. 4a, in the first tier, SR biomarkers can be analyzed on a global basis in a combined SR biomarker assay by measuring all SR biomarkers in a SR biomarker panel simultaneously by pooling detectable SR biomarker-specific binding molecules together. If a persistent homeostatic perturbation is detected, then an assay of the individual SR biomarkers is performed to measure each SR biomarker individually. From the results of the individual SR biomarker assays, a SR biomarker profile can be constructed, which is useful for a more detailed analysis of the stress. As shown in FIG. 4b, if the result of the SR biomarker assay is the identification of a threat to health, then the sample and the subject from whence it came can be referred for differential diagnosis and therapeutic intervention.

SR Biomarker Binding Molecules

SR biomarkers may be detected using a plurality of SR biomarker-specific binding molecules. SR biomarker-specific binding molecules can include, but are not limited to, antibodies, receptors, and aptamers.

Antibodies may be commercial reagents, or newly developed reagents. To achieve improved measurement of SR biomarkers, new antibodies may be prepared using several specifications: (i) antibodies raised in the same host. Hosts may be mammals or chickens; (ii) antibodies specific for highly conserved epitopes on the SR biomarkers; (iii) antibodies cross-reactive with multiple species; and/or (iv) antibodies reactive with all SR biomarkers under identical immunochemical reaction conditions.

Exemplary antibodies and their optimized concentration for the two different types of SR biomarker assays (i.e., multiple-SR biomarker assay and SR biomarker assay) are shown in FIG. 5. As shown, the antibody levels for the combined SR biomarker assay (a) are optimized for all reference specimens, and the antibody levels for the combined SR biomarker assay (b) are optimized for spotted dolphins (Example 4.) Aptamers that are useful as binding partners in SR biomarker assays may be selected from a random oligonucleotide pool based on (i) high affinity for highly conserved molecular regions in the biomarkers, and (ii) optimal binding to the biomarkers under the specific assay conditions (iii) identical binding conditions for aptamers to all biomarkers.

Signaling

In order to be detectable, the SR biomarker-specific binding molecules must be capable of directly or indirectly being detectable. Detectable signals can include, but are not limited to, photonic, electric, magnetic, or mechanical signals.

Assay Formats

Assays types that are useful to perform SR biomarker assays include, for example, immunochemical staining of cells and tissues, flow cytometry, enzyme linked immunosorbant assays (ELISA), and immunoprecipitation. Immunoassays can be performed as a sandwich assay or a competitive assay. It should be evident that when the SR biomarker is, for example, a protein, any assay that is capable of specifically and sensitively detecting the presence and amount of that protein in a sample can be used in the practice of the present invention based on well known protein assay principles.

SR Biomarker Quantification and Data Analysis

SR biomarker levels can be quantified in assays in which at least one SR biomarker is individually measured. Quantification methods may include subjective and objective methods. Subjective methods may include a visual scoring of colored signals. Objective methods may include computerized image analysis and instrumental counting of magnetic, electric, photonic, mechanical and other signals.

Quantitative SR biomarker measurements (i.e., "raw data") may be processed prior to statistical analysis. Raw data processing methods may include normalization and log-transformation. Normalization may include computing a ratio between raw data and baseline. The baseline may be general, e.g., it may be based on an average across a population of samples from healthy biological subjects/systems. Alternatively, the baseline may be personal, e.g., it may be based on an average across time-series data for samples from one biological subject/system. A plurality of statistical methods may be used to provide classification of homeostatic perturbations, which in turn may be directly related to health changes/health disorders, or disease risk.

Known methods for data analysis include basic statistical methods such as range, average and standard deviation that are useful for analyzing the distribution of one-dimensional data such as individual SR biomarker scores, panel scores and combined SR biomarker scores. Statistical tests such as the Wilcoxon's rank sum test (nonparametric analysis of variance) are useful for evaluation the statistical significance of differences between sets of data, such as SR biomarker scores for control and test samples, and for testing potentially confounding effects of sampling variables.

Spearman's correlation test may be used to test reproducibility of data collection method by comparing fit between duplicate data points. Multivariate statistical methods can also be used for multi-dimensional data such as SR biomarker profiles and SR pathway profiles and may include principal component analysis, hierarchic clustering, regression analysis and neuronal nets. Hierarchic clustering may be used to determine relatedness between SR biomarker/pathway profiles in test and reference samples, e.g. it maybe be used to decide whether a test sample is from a normal or a stressed organism, or it may be used to find out which SR biomarkers or SR pathways have coordinated regulation. Principal component analysis may be used to index variability in SR biomarker/pathway profiles in order to point out most activated biomarkers/pathways that may be indicate the molecular mechanism of homeostatic perturbations. Most variable biomarkers contain most information about homeostatic perturbations and may be used for constructing minimized SR biomarker panels.

As disclosed herein, continual data can be also converted in simple-to-use "negative" and "positive" data based on a cut-off data point calculated as: $C=x+2s$, where x is the average data in control samples and s is the standard deviation of control This categorical scoring provides a simplified interpretation of SR biomarker pool scores that is useful for a rapid sorting of samples into "normal" (negative data) and "stressed" (positive data), when the actual data value is not important. This approach is similar to sorting people into "tall" and "average" based on a cut-off value for the height.

As disclosed herein, data related to SR biomarkers and SR pathways may be fused with non-biomarker data sets in order to obtain improved power of classification and/or improved risk prediction. Non-biomarker data sets provide additional information about biological systems and their environment. Non-biomarker data sets may include health histories and results from a plurality of health and environmental tests. These tests may include blood pressure, cholesterol levels, glucose tolerance, hormonal levels, liver function, infectious agents, genetic tests, cognitive neuropsychological tests, psychological stress tests, or environmental quality tests.

The following description presents an exemplary calculation of an SR pathway profile: SR biomarker profiles are converted into SR pathway profiles using the following formula:

$$Z = \begin{bmatrix} Z_1 \\ \vdots \\ Z_{10} \end{bmatrix} \approx \begin{matrix} Z_1 = f_{1,1}y_1 + f_{1,2}y_2 + \ldots + f_{1,40}y_{40} \\ \vdots \\ Z_{10} = f_{2,1} + f_{2,2}y_2 + \ldots + f_{2,40}y_{40} \end{matrix}$$

or $$Z_{p,i} = \sum_{p=1}^{10} \sum_{i=1}^{40} f_{pi} y_i$$

where;
Z is a SR pathway profile;
$Z_p$ is the SR pathway profile for the p-th pathway, p=1, ..., 10;
$y_i$ is the i-th SR biomarker's score, i=1, ..., 40; and
$f_{pi}$ is a constant that indicates the relatedness between the p-th SR pathway and the i-th SR biomarker.

The $f_{pi}$ value is determined empirically. FIG. 2 shows f values for the 40 preferred SR biomarkers and the 10 universal SR pathways. SR biomarkers with a function in or an association with a SR pathway were assigned f=1, and biomarkers without were assigned f=0. In general, f can have other values than 0 and 1 to indicate different modes of relatedness.

The following description presents an exemplary calculation of a variability index for SR biomarkers, which can be used to construct a SR biomarker profile. As disclosed herein, the multi-dimensional variability of SR biomarkers may be indexed to identify most variable SR biomarkers, which might be useful in constructing minimized SR biomarker panels. The variability index for SR biomarker profiles may be calculated using the following formula:

$$v_i = l_{1i}x_{1i} + l_{2i}x_{2i}$$

where;
$v_i$ is the variability index for the i-th SR biomarker (i=1, ..., 40); and
$l_{1i}$ and $l_{2i}$ are the pc1 and pc2 eigenvalues for the i-th SR biomarker; and
$x_{1i}$ and $x_{2i}$ are the absolute values of pc1 and pc2 eigenvectors for the i-th SR biomarker.

The eigenvalues and eigenvectors related to pc1 and pc2 are determined using principal component analysis of SR biomarker profiles.

The following description presents an exemplary calculation of a variability index for SR pathways. As disclosed herein, the multi-dimensional variability of SR pathways may be indexed to identify the most variable SR pathways, which is useful in revealing the molecular mechanism of homeostatic perturbations. The variability index for SR pathways may be calculated using the following formula:

$$v_p = l_{1p} x_{1p} + l_{2p} x_{2p}$$

where;

$v_p$ is the variability index for the p-th pathway (i=1, ..., 10); $l_{1p}$ and $l_{2p}$ are the pc1 and pc2 eigenvalues for the p-th pathway; and $x_{1p}$ and $x_{2p}$ are the pc1 and pc2 eigenvectors for the p-th pathway.

Sampling

Samples that are useful for performing SR biomarker assays may include biological and non-biological samples. Biological samples may be solids, fluids, secretions, exhalations from live and/or dead biological systems. Fluids may include saliva, sweat, tears, breast milk, vaginal secretions, semen, urine, blood, plant sap, natural cellular suspensions, manufactured cell suspensions. Solids may include body tissues, eggs (birds, amphibians, fish, or invertebrates), and microbial bodies (molds, mushrooms, microbial mats, or plankton). Non-biological samples may include materials that might have been previously associated with, and modified by, biological systems including stromatolites, fossils, or materials of nonterrestial origin. Samples may be collected and processed using a plurality of known methods.

Samples can be obtained from any of a number of different sources, such as cells, tissues, and/or an organism such as a vertebrate organism. The vertebrate organism can be a fish, an amphibian, a reptile, a bird, or a mammal. If the vertebrate organism is a mammal, it can be a human or a dolphin, or a socially or economically important mammal selected from the group consisting of a dog, a cat, a cow, a sheep, a pig, a horse, a donkey, a mule, and a goat. If the vertebrate organism is a bird, it can be a socially or economically important bird selected from the group consisting of a chicken, a turkey, a duck, a goose, a pigeon, a parrot, and a parakeet. Alternatively, the bird can be a bird normally living in the wild. Alternatively, the organism can be a plant, such as a socially or economically important plant selected from the group consisting of wheat, corn, rye, oats, barley, lettuce, cabbage, apples, potatoes, tomatoes, peas, oranges, pineapples, lemons, grapes, plums, pears, and bananas. In another alternative, the organism can be an alga.

Assay Devices

The SR biomarker assays described herein can be adapted to be performed by lay users without a laboratory. The users may be health care professionals in point-of-care facilities or lay consumers in field conditions. The devices may have multiple embodiments including single-use devices, simple reusable devices and computerized biomonitors. The single-use devices, similar to over-the-counter lateral flow assays for pregnancy, enable subjective multi-SR biomarker assays to be performed that indicate general stress, such as that caused by a health disorder or the risk or absence thereof. Simple reusable devices also enable objective SR biomarker assays that provide a refined or enhanced indication of stress, and may also enable remote data processing Assay Kits Another aspect of the present invention is that the SR biomarker assay can be provided in a kit which allows for more convenient laboratory-based SR biomarker analysis. The kits may include a plurality of components including reagents, supplies, written instructions, and/or software. The kits may have a plurality of embodiments including laboratory kits and mail-in kits.

Laboratory SR biomarker assay kits may enable tests for individual and/or multi-SR biomarker in a laboratory. The kits may have a plurality of embodiments based on applications and methods for biomarker detection. The kits may also be designed for use with a plurality of samples including exhaled breath, bodily fluids and secretions, tissues, cultured cells. Kit components can include: (1) sampling supplies and instructions; may include sample collectors and storage containers, sample processing tools, fixatives and user instructions; (2) controls; may be biological or synthetic samples of tissues or biofluids with baseline and elevated biomarker levels; and (3) biomarker-binding molecules including antibodies, aptamers, receptors, or other specific binding partners.

SR biomarker-specific binding molecules may be provided as pre-made, ready-to-use reagents for detecting individual or combined SR biomarkers. The reagents may be optimized for tissue-specific applications. Alternatively, SR biomarker-specific binding molecules may be provided as concentrated reagents with suggested working concentrations for different applications. A pair of SR biomarker-specific binding molecules may be provided to enable double-positive SR biomarker recognition. Conjugated SR biomarker-specific binding molecules may also be provided, such as SR biomarker-specific binding molecules conjugated to biotin, fluorescent dyes or quantum dots.

The kits can include secondary reagents. Secondary reagents may be antibodies, enzymes, labels, or chemicals and may enable a complete SR biomarker panel assay.

The kits can further include software. Software may include a training video that may provide additional support including demonstration of SR biomarker assays, examples of results, or educational materials for performing SR biomarker assays.

Mail-in SR biomarker assay sample collection kits enable sample collection and shipment to a remote laboratory for testing. The remote laboratory may perform SR biomarker assays using assay kits, and provide test results to the user. Potential users include lay consumers, and professional users in the field or point-of-care facility. Mail-in tests may have a plurality of embodiments based on samples and applications. The samples may include body fluids, secretions and tissues from different types of organisms including people, animals, plants, microorganisms. Components can include:

(1) Supplies and instructions for collecting and fixing samples to enable mailing and subsequent laboratory analysis of SR biomarkers. The supplies may include sample collectors, sample processing tools and supplies, fixatives, storage containers. The supplies may enable preparation of stabilized samples of whole biofluids and tissues; or cellular spreads made from biofluids. Technical support via telephone and a website.

(2) Mailing supplies to enable sending samples to a remote laboratory that performs SR biomarker tests. The supplies may be a pre-addressed regular mail envelope.

(3) Results provided by mail. The mail may be a letter, an email, information posted on a website. The website may have health tips and links to health care and product providers. The links may be advertisements.

Exemplary SR Biomarker Assay Kit Format for Humans

The SR biomarker assays can be configured into a test kit for the use at home or in doctor's office including: a small, hand-held device similar to a digital thermometer. The device includes a disposable module for sample uptake and reagent storage (refills sold separately), and a re-usable module for signal detection and result display that may involve optical and electronic components. No training required for sampling and test operation. Real-time results (1-3 minutes). Simple readout of results, e.g. percent above baseline or an artificially color-coded scale from green to red.

Alternatively, this assay can be performed on a test strip. One end is briefly put to mouth to wick up saliva. Result (SR biomarker level) is indicated by a color change in the result area of the strip (litmus test-like). Disposable.

It can also be formatted on a sampling strip (a plastic microscopy slide), a collection cup, a plastic spatula, a small pouch with fixative (alcohol), instructions for making and fixing a saliva smear, a mailing envelope/packaging addressed to testing company. Fixed slides can be send by regular mail (SR biomarkers are stable). The testing company processes the slide and sends results back via self-addressed envelope and/or the results are posted on the testing company's website (via personalized access code).

Software, or a web access to the testing company website, with regularly updated information on health-promoting and health-risk factors that can be detected by the SR biomarker assay, health tips, and links to health products and services (paid ads).

Alternatively, the assay may be configured as a lab test kit including instructions and supplies for preparing saliva smears on microscopy slides. Alternatively, saliva smear could be prepared by a doctor's assistant during a medical exam, fixed with an alcohol spray (like a PAP smear) and send to a processing lab. The kit may include anti-SR biomarker antibodies and instructions for diluting and mixing the antibodies to make the multi-SR biomarker reagent suitable for staining of human saliva. The kit may also include microscopic slides with positive and negative controls (saliva smears with normal and stressed cells) and staining instructions, result interpretation, website link for technical assistance.

This assay configuration is well suited for the following applications:

Consumer diagnostics: Self-administered health test for home use. Personalized monitoring of health risk factors such as diet, exercise, health supplements, urban pollution, pesticides, sun exposure, geographical location, work environment, relationships, etc.

POC diagnostics: Health test administered in doctor's office during routine medical checkups (along with routine vital signs).

Personalized medicine: self-administered stress response test to gauge a patient's reaction to a medical drug (or device). Early identification of adverse effects.

Complementary/alternative medicine (CAM): Currently, there is no widely accepted objective test to measure effects of CAM treatments such as acupuncture, cold laser, homeopathic/herbal supplements, physical therapy, massage, meditation. At present, the outcome of CAM treatments is monitored using self-reported pain, stress, energy levels at each office visit. Objective monitoring is challenging because CAM modalities combine multiple factors with physical, chemical, biological and psychological effects on human physiology. SR biomarkers are optimally suited to monitor CAM effects because they were developed for detecting complex combinations of diverse stressors. SR biomarker assays can be used to for initial assessment of patient's stress level, and to monitor/guide CAM treatments.

Mental health diagnostics and treatment monitoring: Currently, mental health diagnostics is largely based on a battery of neuropsychological tests that cannot provide early, preclinical signatures of mental disorders. Mental disorders are associated with increased levels of chronic physiological stress that can be objectively measured by SR biomarker assays to generate SR biomarker profiles. SR biomarker assay-based classification of demented AIDS patients indicates that saliva-based multi-SR biomarker profiling could be used for early detection of neurodegenerative disorders, before the emergence of neuropsychological cognitive deficits. SR biomarkers detect increased cellular stress in saliva during increased psychological stress. This indicates that SR biomarker assays can be used to measure stress levels as a part of the patient's initial mental health assessment, for early detection of post-traumatic stress disorders (PTSD), and to monitor/guide treatments (drugs, counseling). SR biomarker assays can be particularly useful for PTSD screening in people with high risk (soldiers returning from deployment, battered women).

Dental health: SR biomarker assays of saliva/dental plaque is applicable for early detection of gum disease, a serious disorder linked to increased risk of diabetes and cardiovascular disease. Currently, periodontal disease is diagnosed by dentist based on clinical symptoms, and a molecular test for early detection or prediction is not available. Rapid multi-SR biomarker assays can be delivered in dentist's office during routine oral exams, or could be made into self-administered periodontal test for home use. Including SR biomarkers for the microbial activation pathway might improve the sensitivity of gum disease detection. The SR biomarker assay device might use a dental floss for the collection of saliva plus dental plaque and possibly also to directly indicate test results.

Field diagnostics: Health test administered by non-medical personnel during emergency calls or mass health crises due to natural, industrial and terror disasters civilian (e.g. after Hurricane Katrina).

Occupational safety: health biomonitoring in environments with high levels of physiological stressors (heat, radiation, noise, gravity, oxygen, toxins, pathogens, psychological stress) such as haz-mat personnel, fighter pilots, military and police, astronauts.

Environmental safety: Monitoring health outcomes in people with chronic exposures to industrial chemicals used in industrial and agricultural processes, urban pollution etc. SR biomarker assays can be particularly useful for assessing safety of products with unknown biological effects such as engineered nanoparticles.

Exemplary SR Biomarker Assay Applications

It should be readily apparent that the systems and methods described herein have universal applications to analyzing virtually any type of stress from any source of stress in any organism. The applications listed below are merely representative of the broad range of uses of the present invention.

Health screening: The SR biomarker assays may be used to detect elevated SR biomarkers levels that indicate adverse health changes. Adverse health changes may be a non-specific, pre-disease condition such as stress, or an early-stage of a specific disease. Such health screening may be useful to detect asymptomatic health changes for purposes of classifying difficult-to-define health changes, which may be important for disease risk assessment and disease prevention.

The SR biomarker assay can be performed with non-invasive samples including body fluids and secretions, exhaled breath, tissues. The body fluids may include saliva (people, pets, farm animals) and milk (cattle). Body fluids may be processed into cell smears, cell-free fluids or homogenates. The test may be used during routine (preventative) health exams in human and veterinary medicine, agricultural care, wildlife management.

War veterans screening: The SR biomarker assay can provide early indication of asymptomatic post-traumatic stress disorders and brain trauma in soldiers returning from a deployment in a war. Similar screening tests can be performed in populations who may be subject to similar stressors, such as first responders in a disaster.

Personalized product/procedure safety test: Individuals may have different reactions to products and procedures that the average reaction determined during FDA-required safety testing. The SR biomarker assay can be used for personalized assessment of health care products (drugs, supplements, diets, devices, implants) and procedures (surgery, anesthesia, radiation therapy, imaging; complementary/alternative medical procedures including physical therapy, massage, acupuncture, cold laser, meditation, counseling). Also animal/crop/ecosystem management procedures including habitat change, handling procedures.

Sperm bank test: The SR biomarker assay of semen to assess sperm health can be performed along with conventional methods to assess sperm number, viability, and motility.

Safety test for new products and procedures: The SR biomarker assay can be use to screen candidate products and procedures such as medical drugs, pesticides, water treatments, and guide design changes towards reducing and eliminating stressful biological effects. The SR biomarker assay is applicable at multiple stages of safety testing: in vitro cellular tests, laboratory animal testing, clinical trials, environmental tests in different species. SR biomarkers can be particularly useful for novel products with unknown biological effects such as nanomaterials.

Cancer tests: Cervical cancer screening can be performed by SR biomarker staining of cervical cell smears for improved identification of abnormal cervical cells that would replace or supplement the standard PAP test. Prostate cancer screening can be performed by SR biomarker staining of seminal cell smears for identification of abnormal prostatic cells. Non-invasive cancer screening can be conducted by performing SR biomarker assays of saliva for detecting asymptomatic cancers. Detection of cancer and micrometastatic disease in blood samples, biopsy tissues and tumor tissues, is enhanced by supplementing standard cancer tests with SR biomarker assays.

Water quality test: SR biomarkers are applicable to aquatic microorganisms (algae, fungi, protozoa, bacteria). SR biomarkers in aquatic microorganisms are inducible by a variety of physical, chemical and biological water quality factors including temperature changes, oxygen levels, chemical pollutants, biotoxins, pathogens, pH changes. Multi-tier biomarker sensors may be deployed in situ, to monitor SR biomarker levels in freshwater reservoirs and water-treatment facilities.

Prenatal health tests: SR biomarker assays of embryonic cells obtained during in vitro fertilization and amniotic sampling, supplementing standard genetic testing can be use to enhance prenatal testing.

Differentiation between outcomes of health disorders: SR biomarker assay can also be useful in discriminating between progressive and non-progressive forms of disease. A progressive form of a disease is more severe and widespread (e.g. metastatic cancer) and therefore likely to be associated with a different SR biomarker signature than a non-progressive form of the disease. SR biomarker assays can discriminate between prostate tumor cells with low and high Gleason scores. The Gleason score is a traditional method for discriminating between prostate tumors with low and high disease severity. SR biomarker assays can also discriminate between brain cells from AIDS patients with and without cognitive deficits. Cognitive deficits are a traditional method for identifying a more progressive form of AIDS, so-called neuroAIDS.

Diagnostic and therapeutic target identification: SR biomarker assays can indicate preferred biological targets of environmental stressors and/or disease-related stressors that can be used for early detection of stressors, for improved protection against stressors, and for monitoring stress mitigation measures. Increased levels of SR biomarkers may show which species in ecosystems, and cells in organisms, were preferred targets of stressors, i.e. most impacted by stressors, most stress sensitive ("canary in a coalmine"). For example, using the methods of the present invention, keratinocytes are the preferred target of environmental stressors and disease in the skin. Tumor cells with high Gleason score and interepithelial neoplasia (PIN) cells are preferred targets of prostate cancer in the prostate. Glandular epithelial cells were the preferred target of breast cancer in the breast; such cells are also the preferred target of HIV and HTLV in the breast. Multiple cell types and microanatomical areas in the brain were shown to be targeted in AIDS. In case of beta-endorphin (a preferred SR biomarker), the targeted cell was shown to be perivascular microglia in the gray matter of frontal cortex. Salivary epithelial cells and microbial cells were shown to be the preferred target during grieving stress.

Therapeutic agent screening: SR biomarker assays can be used to screen agents for their ability to alter homeostasis. The agent to be screened can be a protein, a peptide, a peptidomimetic, a nucleic acid, a steroid, an alkaloid, a terpene, a monosaccharide, a disaccharide, a carbohydrate larger than a disaccharide, an amino acid or derivative thereof, a nucleic acid base, a nucleoside, or a small molecule that is other than a steroid, an alkaloid, a monosaccharide, a disaccharide, a terpene, an amino acid or derivative thereof, a nucleic acid base, or a nucleoside

EXAMPLES

Example 1

Construction of a SR Biomarker Panel

This experiment provides an exemplary method for constructing a SR biomarker panel that is useful for a broad-based analysis of persistent homeostatic perturbations (i.e., "stress"). Although as described below, expression levels of SR biomarker proteins are exemplified, the same assay principles could easily be adapted to a nucleic acid-based assay to measure, for example, mRNA encoding these proteins, which one would expect to be up-regulated when the associated SR pathways were activated.

Candidate SR biomarkers, Approximately 2000 articles related to stressor effects on humans, animals, plants and microorganisms were compiled from peer-reviewed scientific literature. Meta-analysis of the articles was used to select candidate biomarkers based on two criteria:

(1) Association with one or more universal SR pathways.
(2) Expression in multiple species of animals. Preferred candidate biomarkers were expressed in all taxonomic groups (vertebrate animals, invertebrate animals, protists and fungi, plants and bacteria.)

Assay Format. Immunochemical staining was chosen as a practical assay for the measurement of SR biomarkers, because methods and reagents for immunoassays are readily available and economical. To facilitate reactivity with candidate SR biomarkers and control molecules in different types of samples, the antibodies used for the immunoassay were known to be cross-reactive with many taxonomic groups of animals, and known to react with routinely preserved tissues (fixed in formalin, stored at room temperature.) The description and optimal concentrations of antibodies against 40 SR biomarkers are listed in FIG. 5 ("single antibody.)

Assay Samples. The skin was chosen as a practical sample for broad-based stress analysis, because skin microsamples can be obtained from humans as well as from animals using standard, minimally invasive biopsy procedures. Skin microsamples (3×2×2 mm) were obtained from 85 reference subjects with known health status—38 subjects were stressed, 47 were healthy (control). The stressed subjects were exposed to 30 different stressors; 18 of the stressed subjects had clinical symptoms (e.g. a wound, emaciation or disease-specific symptoms), and 20 subjects had no visible impairments (asymptomatic or pre-symptomatic stress). The stressors included physical stressors (e.g., hypothermia and uv light exposure), chemical stressors (e.g., hypoxia), biological stressors (viral, bacterial and fungal infections; cancer, autoimmune disease; a genetic bone defect; tissue injury; starvation; and strenuous exercise) and psycho-social stressors (restraint, defeat, social disorganization, and mother-child separation.) To broadly cover the biological effects of stressors, the reference subjects represented both genders, four age groups (infant, juvenile, adult, old age) and 8 species (humans and seven species of wild dolphins and whales). The nonhuman animals were accidentally stressed by adverse environmental conditions or human activities, and were used to cover stressors that cannot be ethically studied in medical or laboratory animal experiments, and stressors that are currently uncommon or unknown in humans and laboratory animals (e.g. morbillivirus and dolphin pox.) The control subjects were healthy and not exposed to chronic stress.

SR Biomarker Selection. Three criteria were used to select biomarkers suitable for the skin immunoassays:

(1) The biomarker expression was consistently located in the top layer of the skin (the epidermis) indicating that only the surface layer of the skin (3 mm skin depth in humans) can to be sampled for the assay.

(2) The biomarker expression was ubiquitous in the epidermis (i.e. found in nearly all cells) sampled at different body sites, indicating that only a very small area (2×2 mm) was necessary for the assay, and the sampling site could be variable.

(3) The biomarker expression level was abundant, indicating that biomarker levels could be accurately measured using standard immunohistochemical staining ("HIS") methods (i.e. without signal amplification.) Preferred biomarkers met all criteria.

SR Biomarker Measurements. Quantitative immunochemical measurements of the 40 SR biomarkers were obtained to evaluate whether they were modulated by stress. To ensure comparable measurements, each SR biomarker was measured in all reference samples in the same immunochemical experiment, and all antibodies were applied using identical reaction conditions (buffer, reaction time and temperature.) The staining intensity (SI) was quantified using image analysis (Image-Pro Plus 4.1 software, Media Cybernetics, Silver Spring, Md.; Olympus BX50 microscope with DVC camera 1310C, Scientific Instrument Company, Sunnyvale, Calif.). Images were captured at ×100 magnification using identical microscope and camera settings. SI was computed as SI=MOD×PA, where "MOD" is the mean optical density and "PA" is the percentage of the stained area. MOD was measured by applying a color file to the stained area of the image. To ensure comparable MOD counts, the same color file was applied to all samples.

For each skin sample, a SI measurement was calculated as the average for 3 representative images of the sample. This method for collecting SI measurements was highly reproducible (Spearman rank correlation coefficient r=0.98, p<0.001 for duplicate scoring of 20 samples.) To facilitate statistical analysis, the SI measurements for each biomarker were divided by the average SI measurement of that biomarker in control samples (normalization), and log-transformed. Base 3 was used for the logarithmic transformation because experts in visual scoring of immunochemical staining typically assume that a 3-fold difference in the staining level is meaningful. The normalized and log-transformed Si measurements are referred to herein as the "SR biomarker scores." Based on the normalization and the base 3 log scale, score 0 represents the baseline, score 1 represents 3-fold increase relative to the baseline etc.

Figure 7:
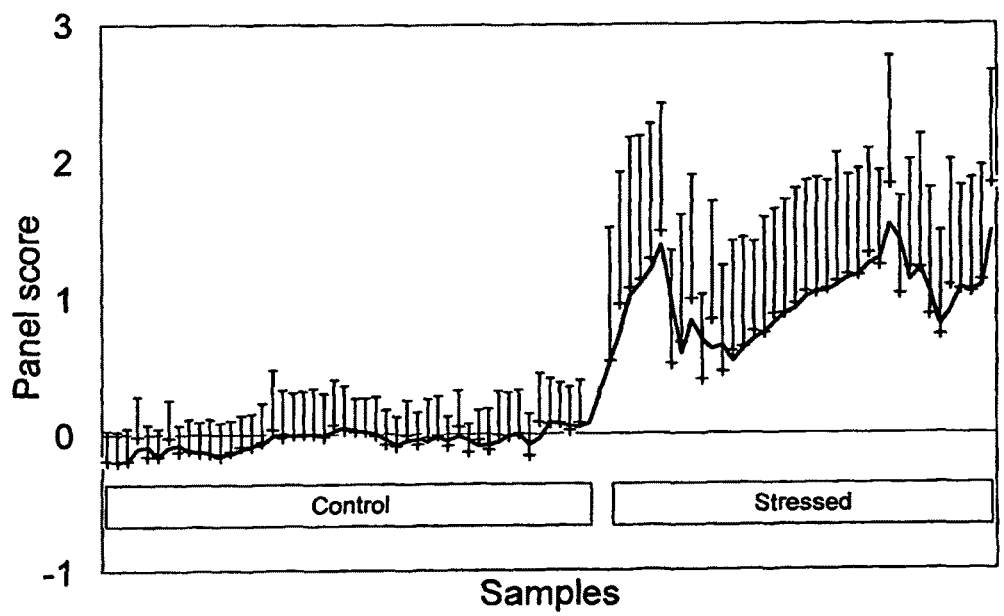
FIG. 7 depicts SR biomarker panel scores in reference skin samples. Category axis, reference skin samples from control and stressed subjects. Value axis, panel scores calculated as the average across 40 SR biomarker scores. The scores are in a log scale, base 3. Score 0 corresponds to a baseline, scores 1, 2 and 3 correspond to 3-fold, 9-fold and 27-fold increases relative to the baseline. Error bars are standard deviations.

FIG. 7 shows that the average expression level of the 40 SR biomarkers in control samples was near baseline, demonstrating that SR biomarker levels were not elevated in normal subjects. Surprisingly, the average level of all selected SR biomarkers in samples from stressed subjects was 2-7 fold higher than baseline and highly fluctuated from sample to sample, which demonstrated that the biomarker levels were more strongly elevated in some, but not all, samples. As will be explained below, the fluctuations from sample to sample in this experiment, which relate primarily to differences in the source of stress, are useful to construct profiles that are helpful to analyze the nature and characteristics of the stress.

Figure 8:
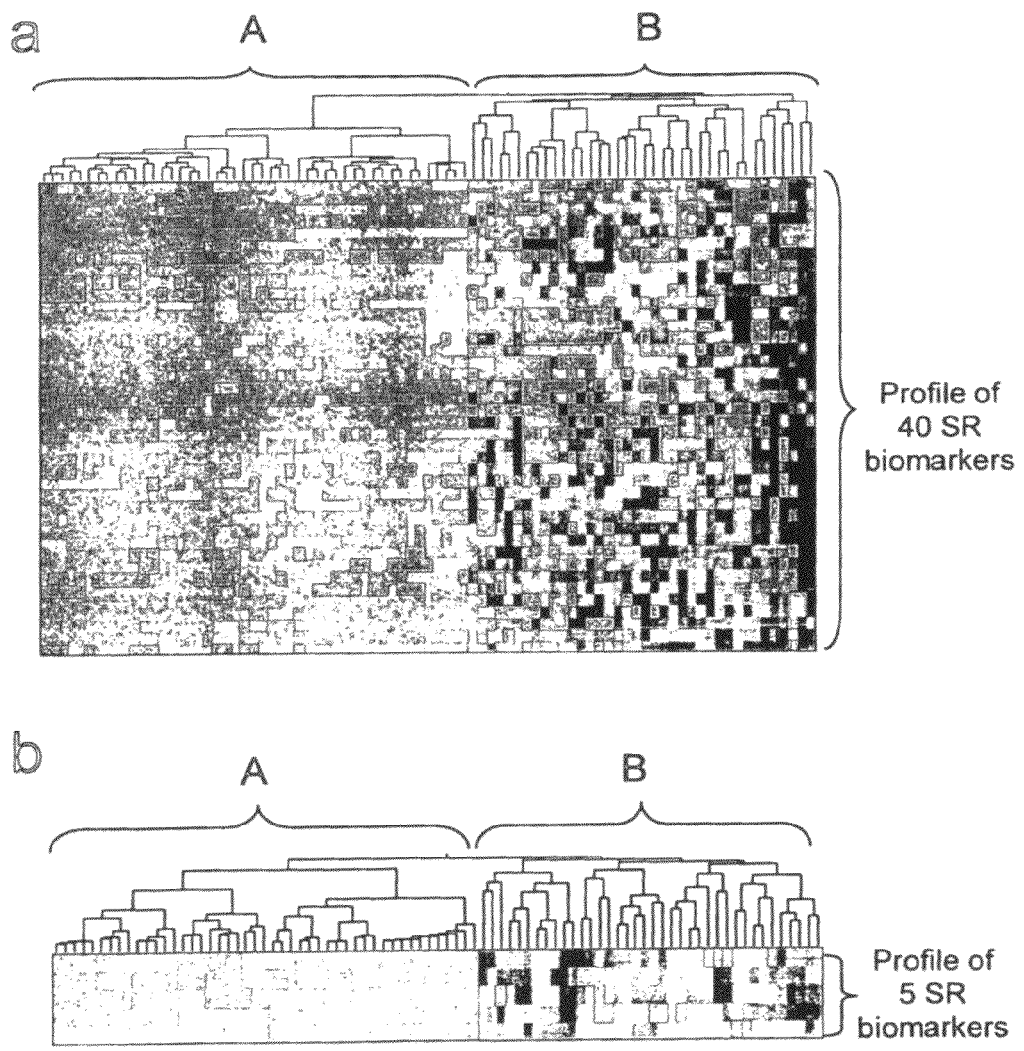
FIG. 8 depicts SR biomarker profiles in reference skin samples. Hierarchic clustering of the profiles is shown. Similar profiles are in clusters, and the length of dendrogram branches is proportional to relatedness between the profiles.

SR Biomarker Panel Validation. As described above, the panel of 40 individual SR biomarkers is multi-dimensional—it is generic to multiple organisms and multiple stressors. To simply assess the classification power of the panel for stress (i.e., the ability of the panel to be useful to distinguished abnormal from normal samples), a "panel score" was calculated as the average of all 40 biomarker scores for each sample. FIG. 8 shows that the panel scores were elevated in all stressed samples documenting that the biomarker panel was broadly sensitive to different types of stress. The results are summarized in Table 3 below.

TABLE 3

| | Panel scores | | | |
|---|---|---|---|---|
| Sample | N | Range | Mean | St. Dev. |
| Control | 47 | −0.20 to 0.09 | −0.05 | 0.08 |
| Stressed | 38 | 0.4 to 1.83 | 1.00 | 0.32 |

The panel scores for stressed and control samples were significantly different (Wilcoxon's rank sum test, p<0.001), and not affected by sampling variables (Wilcoxon's rank sum test of gender, age and species, p=0.82, 0.80 and 0.05, respectively.)

SR Biomarker Profiles. Panel scores provide only a coarse measure of the information derived from measurement of all 40 SR biomarkers individually. When evaluated individually for each sample, a "profile" emerges from the pattern of SR biomarker scores, i.e., a SR biomarker profile. As shown in FIG. 9a, each SR biomarker score is translated to a grey-scale value, and each column of grey-scale values represents a "SR biomarker profile" for the control samples (left side, generally lighter grey-scale values) and stressed samples (right side, generally darker grey-scale values.)

SR Biomarker Clustering. To utilize the full information content of the SR biomarker profile, multivariate statistics can be utilized, i.e., a 40-dimensional vector whose individual components are the 40 individual SR biomarker scores. This method is used to determine the relatedness between the vectors using hierarchic clustering. Results of the clustering of the SR biomarker panels in the reference samples are also shown in FIG. 9a. As shown, the length of dendrogram branches is proportional to relatedness of the SR biomarker profiles, and similar profiles are grouped together in clusters. FIG. 9a clearly shows that SR biomarker profiles in control and stressed samples formed two separate clusters (A and B). This results demonstrates that the 40 SR biomarker panel distinguished stressed samples from control samples with 100% reliability.

Example 2

Construction of a Minimized SR Biomarker Panel

In this Example, the 40 SR biomarker panel described in Example 1 was used to construct and validate a minimized panel of 5 SR biomarkers that was capable of classifying the reference samples with the same reliability as the 40 SR biomarker panel.

Selection of SR Biomarkers Based on High Score Variability. The variability of SR biomarker scores in reference samples from control versus stressed subjects was determined using principal component analysis. The first two principal components, pc1 and pc2, cumulatively accounted for >97% of the variability. The variability index was calculated as:

$$v_i l_{1i} x_{1i} + l_{2i} x_{2i}$$

where;

$v_i$ is the variability index for the i-th SR biomarker (i=1, ..., 40);

$l_{1i}$ and $l_{2i}$ are the pc1 and pc2 eigenvalues for the i-th SR biomarker; and $x_{1i}$ and $x_{2i}$ are the absolute values of pc1 and pc2 eigenvectors for the i-th SR biomarker.

The variability index, $v_i$, for the 40 SR biomarkers is in Table 4 below.

TABLE 4

Variability Index for SR Biomarker Scores

| # | SR Biomarker | Variability Index |
|---|---|---|
| 17 | HSF-1 | 6.413 |
| 37 | SOD Cu | 5.776 |
| 27 | Mekk-1 | 5.552 |
| 36 | SOD Mn | 5.389 |
| 8 | Ferritin | 5.062 |
| 14 | Hsp40 | 4.990 |
| 1 | Endorphin | 4.951 |
| 33 | Serotonin R | 4.568 |
| 9 | GR | 4.561 |
| 29 | CYP red | 4.414 |
| 13 | Hsp25/27 | 4.347 |
| 2 | Caspase 8 | 4.258 |
| 18 | HO-1 | 4.236 |
| 26 | MT | 4.063 |
| 11 | Grp75 | 4.018 |
| 40 | VIP | 3.983 |
| 28 | Mek-1 | 3.966 |
| 35 | Sustance P | 3.910 |

TABLE 4-continued

Variability Index for SR Biomarker Scores

| # | SR Biomarker | Variability Index |
|---|---|---|
| 25 | Leptin R | 3.881 |
| 20 | IL-6 | 3.844 |
| 30 | iNOS | 3.786 |
| 16 | Hsp90 | 3.711 |
| 5 | CYP450 | 3.642 |
| 4 | Cox-2 | 3.507 |
| 34 | Serotonin | 3.471 |
| 31 | Fos | 3.433 |
| 6 | Cyt c | 3.393 |
| 23 | IL-12 | 3.300 |
| 10 | Grp58 | 2.913 |
| 38 | TGF | 2.877 |
| 12 | GST | 2.850 |
| 32 | Jun | 2.660 |
| 15 | Hsp60 | 2.595 |
| 19 | IL-1 | 2.483 |
| 22 | IL-10 | 2.446 |
| 3 | Cyclin | 1.961 |
| 7 | EGFR | 1.758 |
| 21 | IL-8 | 1.619 |
| 24 | Laminin | 1.613 |
| 39 | p53 | 1.388 |

The five SR Biomarkers with highest variability index values were selected to construct a minimized SR biomarker panel. The classification power of the minimized panel was determined using hierarchic clustering. FIG. 8b shows that the five SR Biomarkers with the highest variability index values (HSF-1, SOD Cu, Mekk-1, SOD Mn, ferritin from top to bottom in FIG. 8b) are sufficient to classify reference samples as coming from stress or normal subjects (i.e., "classifying stress") with the same 100% reliability as the 40 SR biomarker panel in FIG. 8a. The top four or the top three biomarkers provide 98.8% reliability (1 false negative), the top two provide 97.6% reliability (2 false negatives) and the top one SR biomarker (HSF-1) provides 84.7% reliability (13 false negatives) for classifying stress. Also as depicted in FIG. 8, each SR biomarker profile (i.e., each column of grey-scale values) provides a useful characterization of stress response activation in each individual sample tested.

Example 3

SR Pathway Profiles for Analyzing Molecular Mechanisms of Stress

In addition to the SR biomarker profiles described above in Examples 1 and 2, SR pathway profiles can also be constructed to more particularly analyze the molecular mechanisms of stress in differentially activating individual SR pathways.

SR Pathway Profile Construction. To determine the molecular mechanism of stress, "pathway activation analysis" was performed. The principle of this analysis is the conversion of a SR biomarker profile into a "SR pathway profile" (FIG. 1.) SR pathway profiles are useful as indicators of the molecular mechanism of stress by revealing which SR pathways are most activated and which SR pathways have a coordinated regulation. SR pathway profiles can also be used for classifying samples as being from normal versus stressed subjects in the same manner as SR biomarker profiles.

SR pathway profiles were calculated using the following formula:

$$Z = \begin{bmatrix} Z_1 \\ \vdots \\ Z_{10} \end{bmatrix} \approx \begin{matrix} Z_1 = f_{1,1}y_1 + f_{1,2}y_2 + \ldots + f_{1,40}y_{40} \\ \vdots \\ Z_{10} = f_{2,1} + f_{2,2}y_2 + \ldots + f_{2,40}y_{40} \end{matrix}$$

or $$Z_{p,i} = \sum_{p=1}^{10} \sum_{i=1}^{40} f_{pi} y_i$$

where;
Z is a SR pathway profile;
$Z_p$ is the SR pathway profile for the p-th pathway, p=1, ..., 10;
$y_i$ is the i-th SR biomarker's score, i=1, ..., 40; and
$f_{pi}$ is a constant that indicates the relatedness between the p-th SR pathway and the i-th SR biomarker.

The $f_{pi}$ value is determined empirically. FIG. 2 shows f values for the 40 preferred SR biomarkers and the 10 universal SR pathways. As shown, SR biomarkers with a known function in or association with a SR pathway were assigned f=1, and biomarkers without a function were assigned f=0. In general, f can have values other than 0 and 1 to indicate different modes of relatedness.

Activation of SR pathways. The activation level of individual SR pathways was indexed based on the SR pathway variability. The variability was determined using principal component analysis as described for the SR biomarker scores in Example 2.

The variability index was calculated as:

$$v_p = l_{1p} x_{1p} + l_{2p} x_{2p}$$

where;
$v_p$ is the variability index for the p-th pathway (i=1, ..., 10);
$l_{1p}$ and $l_{2p}$ are the pc1 and pc2 eigenvalues for the p-th pathway; and
$x_{1p}$ and $x_{2p}$ are the absolute values of pc1 and pc2 eigenvectors for the p-th pathway.

The variability index for the 10 SR pathways in the 85 reference skin samples (see Example 1) is in Table 5 below.

TABLE 5

Activation of SR Pathways

| | SR Pathway | Variability Index |
|---|---|---|
| 1 | Redox | 1.935 |
| 2 | Xenobiotics | 1.796 |
| 3 | Chaperoning | 2.008 |
| 4 | DNA repair | 1.800 |
| 5 | Cell adhesion | 1.747 |
| 6 | Cell growth | 1.751 |
| 7 | Cell death | 1.754 |
| 8 | Neuro-endocrine signaling | 1.780 |
| 9 | Immunity | 1.802 |
| 10 | Microbial activation | 1.825 |

The variability index showed that the pathways 1, 3 and 10 (underlined) were preferentially activated by diverse stressors in humans and animals. This result surprisingly indicates that the dominant molecular mechanism of stress in the skin involves misfolded proteins (the trigger for pathway 3), increased free radicals (the trigger for pathway 1) and increased activation of commensal and pathogenic microorganisms (the trigger for pathway 10).

As shown above, the pattern of variability index data from all of the ten SR pathways can form the basis for construction of a SR pathway profile.

Figure 9:
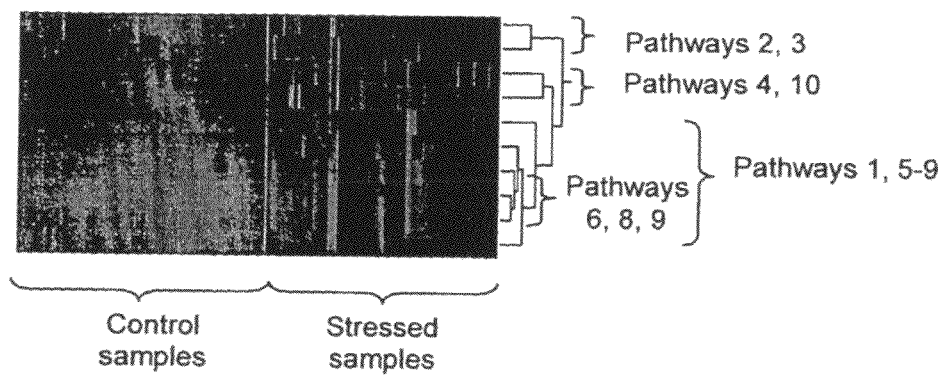
FIG. 9 depicts SR pathway profiles in reference samples. The profiles represent ten SR pathways listed in FIG. 2. Hierarchic clustering of the profiles is shown. Similar profiles are in clusters, and the length of dendrogram branches is proportional to relatedness between the profiles. Small brackets on the right show SR pathways that have similar profiles indicative of coordinated regulation. Large brackets on the bottom show that control and stressed samples are in separate clusters indicating that SR pathway profiles classified stress with 100% reliability.

Coordinated Regulation of SR Pathways. Hierarchic clustering of SR pathway profiles was performed to find out which SR pathways had similar activation patterns in stressed samples. SR pathways with similar activation patterns are likely to have coordinated regulation. Hierarchic clustering shows pathways with similar activation patterns as clusters, the length of the dendrogram branches being proportional to the relatedness in activation patterns. FIG. 9 shows hierarchic clustering of 10 SR pathways in the reference skin samples. The results indicate coordinated regulation of: (i) pathways 2 and 3, (ii) pathways 4 and 10, (iii) pathways 1, 5, 6, 7, 8 and 7, and particularly pathways 6, 8 and 9. FIG. 9 also shows that SR pathway profiles discriminated between stressed and control samples with the same 100% reliability as the SR biomarker profiles in FIG. 8.

Resolution of SR Pathway Profiles. SR pathway profiles can be constructed at different resolution levels to represent effects of (i) different stressors (a panoramic profile of stress shown in this Example), (ii) one stressor in many subjects (an average profile, for example of stress related to prostate cancer in Example 5) or (iii) one stressor in one subject (a personalized profile, for example of stress related to prostate cancer in Example 5.)

Example 4

Combined SR Biomarker Assay for Stress Screening in Dolphins

Wild spotted dolphins in the Pacific Ocean have been chased and captured in nets during commercial fishing operations since the 1950s, and currently the dolphin population originally estimated as 5 million was reduced to a fraction of its original size. It is not known how the fishing operations might affect dolphin health and longevity. Current methods for assessing the health of a population are based on estimated trends in abundance, mortality, and reproductive rates. These methods are too slow to provide early warnings of compromised health in species with long generation times, such as the dolphin. Therefore we used a new method, the stress response profiling, to obtain early warnings of compromised health due to stress.

To rapidly and economically screen the 40 SR biomarker panel in a large set of dolphin samples, the combined expression level of all 40 SR biomarkers was measured using pooled anti-SR biomarker antibodies The resulting measurement was called a combined SR biomarker score. This constitutes a "Tier 1" assay as depicted in FIG. 4.

Figure 10:
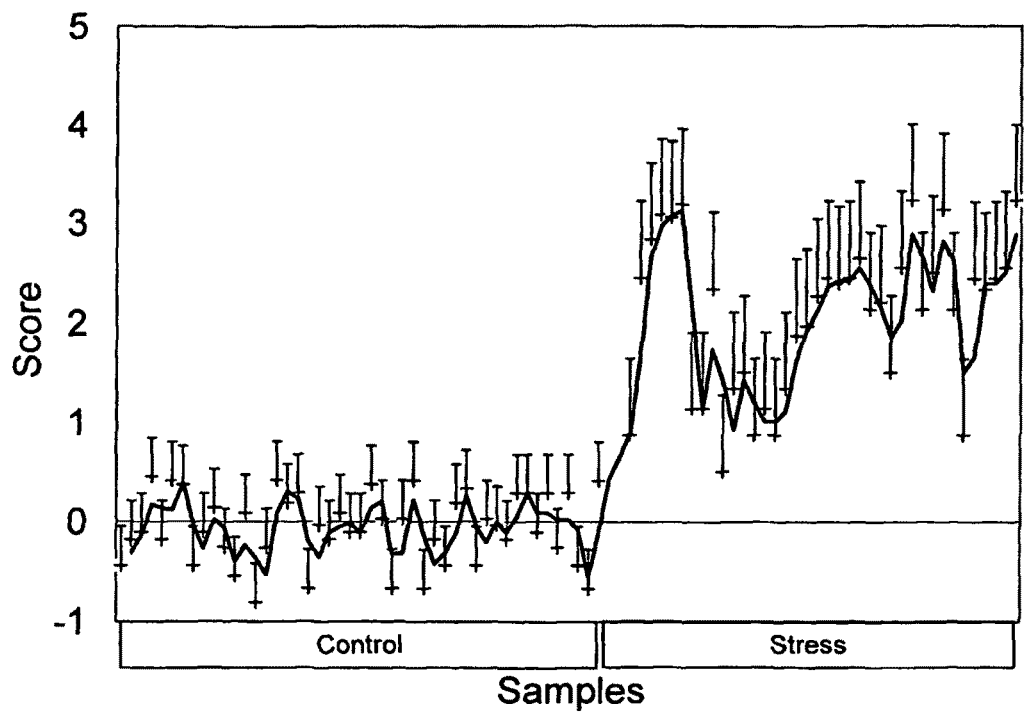
FIG. 10 depicts combined SR biomarker scores in reference skin samples. Category axis, reference skin samples from 47 control and 38 stressed subjects. Value axis, scores for 40 combined SR biomarkers determined using immunohistochemical staining with pooled antibodies. The scores are in a log scale, base 3. Score 0 corresponds to a baseline, scores 1, 2 and 3 correspond to 3-fold, 9-fold and 27-fold increases relative to the baseline. Error bars are standard deviations.

The reference skin samples described in Example 1 were used to validate the combined SR biomarker assay as a tool for discriminating between samples from stressed and control subjects. Optimal concentrations of pooled antibodies against 40 SR biomarkers are listed in FIG. 5 ("Antibody pool$^{a}$".) The immunohistochemical staining, the image analysis and the conversion of the staining intensity measurements into normalized, log-transformed scores was performed as described in Example 1. Combined SR biomarker scores were about 9-fold higher in stressed samples than in control (see FIG. 10 and Table 6 below.) The difference was statistically significant (Wilcoxon's rank sum test, p<0.001) and not affected by gender, age and species (Wilcoxon's rank sum test, p=0.73, 0.80 and 0.25, respectively).

TABLE 6

Combined SR Biomarker Scores

| Sample | N | Range | Mean | S.D. | Positive | Negative |
|---|---|---|---|---|---|---|
| Control | 47 | −0.93-0.53 | −0.07 | 0.39 | 0 | 47 (100%) |
| Stressed | 38 | 0.71-3.24 | 2.09 | 0.77 | 38 (100%) | 0 |

Figure 6:
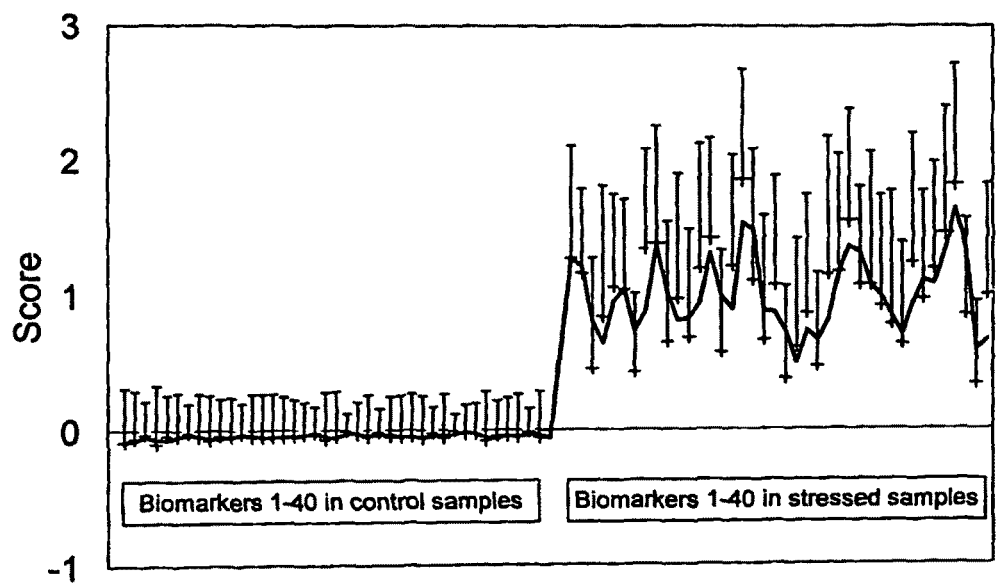
FIG. 6 depicts average SR biomarker scores in reference skin samples. Category axis, SR biomarkers 1-40 as listed in FIG. 2. Value axis, the average scores for individual SR biomarkers across control and stressed samples. The scores were determined using immunohistochemical staining and are in a log scale, base 3. Score 0 corresponds to a baseline, scores 1, 2 and 3 correspond to 3-fold, 9-fold and 27-fold increases relative to the baseline. Error bars are standard deviations.

As shown, the combined SR biomarker scores strongly correlated with the panel scores for the 40 SR biomarker panel described in Example 1 and FIG. 6 (Spearman's rank correlation coefficient r=0.86, p<0.001).

Combined SR biomarker scores were divided into "negative" and "positive" based on a cut-off score calculated as: C=x+2s, where x is the average score in control samples and s is the standard deviation of control scores. In reference samples, x=0.07, s=0.39, C=0.71, negative scores were <0.71 and positive scores were ≧0.71, see Table 6. This categorical scoring provides a simplified interpretation of combined SR biomarker scores that is sufficient for a rapid sorting of samples into "normal" (negative scores) and "stressed" (positive scores), when the actual score value is not important. This approach is similar to sorting people into "tall" and "average" based on a cut-off value for the height.

The combined SR biomarker scores were measured in 868 skin samples from wild spotted dolphins using the same immunoassay assay methods as in Example 1. Optimal concentrations of pooled anti-SR biomarker antibodies for the spotted dolphin samples are listed in FIG. 5 ("Antibody pool$^{b}$".) Categorical scores were assigned using the same formula for calculating the cut-off score as described for the reference samples above. Samples with a statistically normal distribution of scores (n=142) were designated as "normal" samples. In these samples, x=1.17, s=0.44 and C=2.06. Based on the cut-off score, scores in the 868 dolphins were negative if <2.06 and positive if ≧2.06. The categorical scoring was highly reproducible (Spearman rank correlation coefficient r=0.96, p<0.001 for duplicate scoring of 158 samples). The categorical scores are in Table 7 below.

TABLE 7

Combined SR Biomarker Scores in Spotted Dolphins

| Sample | N | Stressor | Positive | Negative |
|---|---|---|---|---|
| Group 1 | 202 | No | 75 (37%) | 127 (63%) |
| Group 2 | 666 | Yes | 562 (84%) | 104 (16%) |
| Group 3a | 70 | Low | 0 | 70 (100%) |
| Group 3b | 354 | High | 354 (100%) | 0 |

In Table 7, the dolphins are divided into two groups based on exposure to the stressor (i.e., the fishery.) The stressor exposure was estimated based on the known amount of fishing operations in the geographical areas where the dolphins lived, and on the dolphin behavior, which is modified by the fishery exposure. Table 7 shows that Group 2 that was exposed to the fishery had a higher frequency of positive scores than the unexposed Group 1. The difference was significant (Fisher's test, p<0.001.)

To investigate cumulative effects of repeated involvement in the fishery, 424 dolphins from the Group 2 were designated as Group 3 and the amount of fishing operations was indexed in the geographical areas where the dolphins were sampled. Table 7 shows that dolphins with positive scores were found in geographical areas with high numbers of fishing operations. The positive correlation between the cumulative amount of the stressor and the frequency of positive scores was significant (Wilcoxon's rank sum test, p=0.0382.) These results show that the commercial fishery might be causing stress in spotted dolphins, and the stress is proportional to the cumulative amount of the fishery in the dolphin's habitat.

Example 5

SR Profiling for the Analysis of Stress Related to Prostate Cancer

Prostate carcinoma (PC) is one of the most common human malignancies. Current diagnostic methods for PC include a blood test for the biomarker PSA, and histological tumor grading that provides an index of the malignancy potential of the tumor (the Gleason score), which is used to predict the clinical outcome. Recent efforts in PC research have been focused on the study of genes expressed in PC. However, prostate tumor biology cannot be fully understood at the gene transcription level because gene transcripts typically undergo multiple post-transcriptional and post-translational events before they yield functional proteins that play roles in tumor formation and progression. Consequently, protein-based methods such as the stress response profiling, have a greater potential to bring new insights into PC biology.

A panel of 41 SR biomarkers was applied to 12 prostate biopsy samples from PC patients. Cytokeratin (a positive control) and PSA (the standard PC biomarker) were measured in parallel. The 41 SR biomarkers included the 40 biomarkers described in FIG. 2, and the Hsp 70 biomarker described in FIG. 3. The expression of the SR biomarkers was analyzed using the methods described in Examples 1-4, except that the staining intensity was scored by an expert pathologist using the traditional 0, 1, 2, 3 scoring procedure in which 0 represents a baseline signal and scores 1 to 3 represent 3-fold increases over the baseline. The traditional scoring procedure was highly reproducible (Spearman rank correlation coefficient r=0.92, p<0.001 for duplicate scoring of 20 samples.) Antibodies against the 40 SR biomarkers are described in FIG. 5. The anti-Hsp70 antibody was a mouse monoclonal IgG1 to human hsp70 (SPA-816, Stressgen) diluted 1:100 for the individual detection of Hsp70, and 1:4, 000 for the combined SR biomarker assay.

The SR biomarkers were scored separately in five micro-anatomical areas of the prostate samples: (1) tumor with a high malignancy potential (Gleason score ≧7), (2) high grade intraepithelial neoplasia (PIN) considered to be the precursor of malignant tumors, (3) tumor with a low malignancy potential (Gleason score<7), (4) glandular atrophy, a non malignant disease and (5) stroma which is the surrounding healthy prostate tissue.

Figure 11:
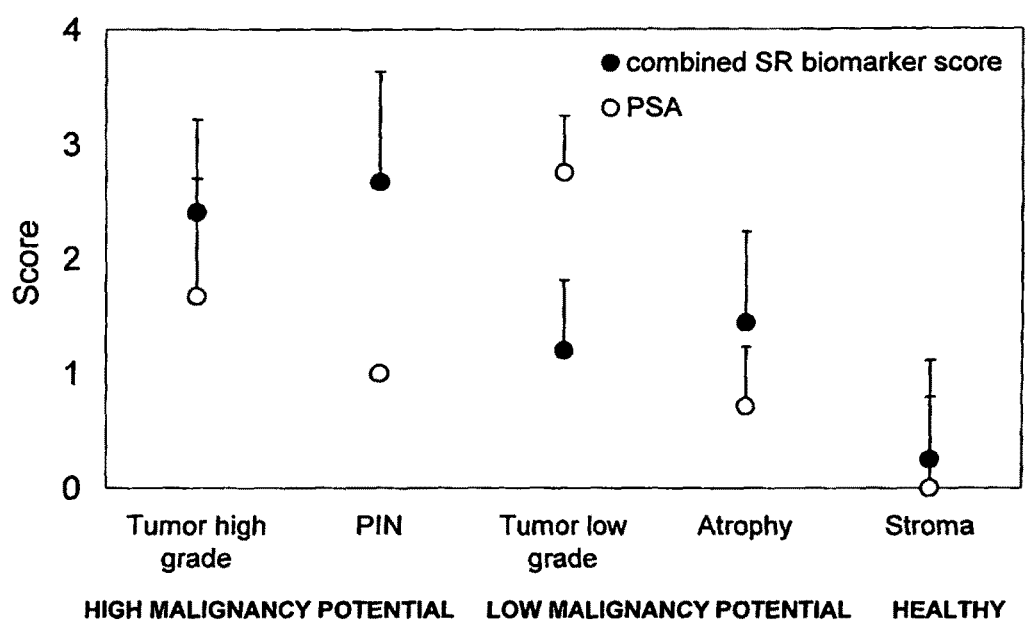
FIG. 11 depicts the expression scores for combined SR biomarkers in prostate cancer patients. Category axis, five micro-anatomical areas of the prostate: high grade tumor and PIN (high malignancy potential), low grade tumor and atrophic glands (low malignancy potential) and stroma (healthy tissue). Value axis, scores for combined 41 SR biomarkers or for PSA, a standard prostate cancer biomarker. The scores are in a log scale, base 3. Score 0 corresponds to the baseline staining in control samples. Scores 1, 2 and 3 and correspond to 3-fold, 9-fold and 27-fold increases relative to the baseline. Error bars are standard deviations.

To rapidly survey stress levels in the samples and to identify most stressed tissue areas, the combined SR biomarker assay was used to measure the combined level of all 41 biomarkers. FIG. 11 shows that the combined levels of SR biomarker levels were 15-25 fold higher in the high grade tumor and PIN, and 3-6 fold higher in the low grade tumor and atrophy, than in the stroma. FIG. 11 also shows that PSA levels were lower in the high grade tumor and PIN than in the low grade tumor. This result demonstrates that the combined SR biomarker level positively correlates with the tumor malignancy potential whereas the PSA level shows a negative correlation, indicating that the SR biomarkers might be better indicators of the clinical PC outcome than PSA.

To classify stress in the five micro-anatomical areas of PC, SR biomarker profiles in the prostate were compared to SR biomarker profiles in the reference skin samples, described in Examples 1 and 2. Hsp70 data were not included in the comparison because this biomarker was not measured in the reference skin samples. All four diseased PC areas (tumors, PIN and atrophy) were classified as stressed whereas stroma was classified as normal. SR biomarker profiles of the malignant areas (high grade tumor and PIN) were similar, and distinct from profiles of the areas with low malignancy potential (low grade tumor and atrophy). Classification based on the 40 SR biomarker panel was similar to results obtained using the minimal 5 SR biomarker panel described in Example 2.

To analyze the molecular mechanism of stress in PC, SR pathway profiles were constructed as described in Example 3. As shown in Table 8 below, pathways 3, 4 and 9 (underlined) were most variable (the average pathway signature of PC-related stress.) This result indicates that the dominant molecular mechanism of stress in prostate cancer involves misfolded proteins (the trigger for pathway 3), DNA mutations (the trigger for pathway 4) and increased stimulation of immune responses (the trigger for pathway 9).

TABLE 8

Variability of SR pathways in prostate cancer

| | | Variability Index | | |
|---|---|---|---|---|
| | SR Pathway | All cases | Case 1 | Case 2 |
| 1 | Redox | 1.79 | 1.54 | 2.05 |
| 2 | Xenobiotics | 1.31 | 1.23 | 1.40 |
| 3 | Chaperoning | 1.99 | 1.82 | 2.18 |
| 4 | DNA repair | 2.00 | 1.96 | 2.03 |
| 5 | Cell adhesion | 1.42 | 1.24 | 1.60 |
| 6 | Cell growth | 1.76 | 1.52 | 2.00 |
| 7 | Cell death | 1.43 | 1.33 | 1.53 |
| 8 | NE signaling | 1.77 | 1.47 | 2.07 |
| 9 | Immunity | 1.82 | 1.55 | 2.08 |
| 10 | Microbial activation | 1.60 | 1.50 | 1.70 |

A comparison between the SR pathway profile of prostate cancer (3, 4, 9) and the SR pathway profile of diverse stressors in reference skin samples (1, 3, in Example 3) shows that the molecular mechanism of stress has universal features (pathway 3 is dominant in both situations) as well as disease-specific features (pathways 4, 9 are most activated by PC and pathways 1, 10 by diverse stressors.) Individual pathway signatures of PC were either the same as the average PC signature (3, 4, 9 in All cases and in Case 1, Table 7) or showed an individual difference in the molecular mechanism of stress (3, 8, 9 in Case 2). Individual differences in the molecular mechanisms of stress could be used for personalized disease management such as a personalized medication strategy.

In conclusion, this experiment demonstrates that the SR profiling methods and the SR biomarker panel constructed using the reference skin samples are directly applicable to prostate samples and relevant to prostate cancer. The results of SR profiling of PC samples provided new information into the molecular biology of PC. This information has practical applications in predicting the malignant potential of a prostate tumor, and in designing and monitoring PC treatments.

Example 6

SR Profiling for the Analysis of Stress Related to Breast Diseases

Five breast biopsy samples were obtained from two cases of breast cancer (BC, invasive ductal carcinoma), one case of breast disease due to a blood cancer caused by a viral infection (ATL, HTLV-associated adult T cell leukemia) and two control cases with benign breast changes (fibroid mastopathy). The expression of a panel of 41 SR biomarkers was analyzed in the breast samples using methods described in Example 5. EMA (epithelial membrane antigen), a conventional biomarker expressed by both normal and diseased mammary epithelial cells, was measured in parallel as a positive control.

To rapidly survey stress levels in different areas of the breast tissue, the combined level of the 41 SR biomarkers were measured using a combined SR biomarker assay. The SR biomarker expression in the breast was consistently found in the mammary epithelium. In the ATL sample, SR biomarkers were also expressed in the large population of infiltrating leukemic T cells that were found within the mammary epithelium. The combined SR biomarker levels were 20-30 fold higher in the BC and ATL samples than in the control breast sample. The EMA levels were high in all samples.

To classify stress in the breast, SR profiles in the breast samples were compared with the SR profiles in the reference skin samples, using methods shown in Example 5. The BC and ATL samples were classified as stressed, and the control breast as normal, by both the 40 and the 5 SR biomarker panels. SR profiles of BC were similar and distinct from the SR profile of ATL.

SR pathway profiling was applied to analyze the molecular mechanism of stress in breast diseases, using the same methods as in Example 5. The variability index for SR pathways is in Table 9 below. It was determined that the molecular mechanism of BC-related stress involves misfolded proteins (the trigger for pathway 3), increased free radicals (the trigger for pathway 1) and changes in cell cycle and growth (the trigger for pathway 6). The mechanism of ATL-related stress was found to involve increased activation of commensal and pathogenic microorganisms (the trigger for pathway 10), increased levels of toxic molecules (the trigger for pathway 2) and increased free-radicals (the trigger for pathway 1).

TABLE 9

Variability of SR pathways in Breast Diseases

| | | Variability Index | |
|---|---|---|---|
| | SR Pathway | Breast cancer | ATL |
| 1 | Redox | 0.89 | 1.13 |
| 2 | Xenobiotics | 0.60 | 1.19 |
| 3 | Chaperoning | 1.07 | 1.08 |
| 4 | DNA repair | 0.87 | 1.11 |
| 5 | Cell adhesion | 0.81 | 0.90 |
| 6 | Cell growth | 0.88 | 1.07 |
| 7 | Cell death | 0.71 | 1.08 |
| 8 | NE signaling | 0.87 | 1.04 |
| 9 | Immunity | 0.84 | 1.08 |
| 10 | Microbial activation | 0.87 | 1.26 |

In conclusion, this experiment demonstrates that the SR profiling methods and the SR biomarker panels constructed using the reference skin samples, are directly applicable to breast samples and relevant to breast cancer and the ATL breast disease. The results provided new information into the biology of these diseases, which might be useful for the development of new diagnostic approaches to BC and ATL (no biomarkers currently available), and in designing and monitoring treatment in these diseases.

Example 7

The Use of SR Biomarkers for the Analysis of Stress Related to NeuroAIDS

The recently introduced highly active antiretroviral therapy (HAART) has not resolved problems of HIV-associated cognitive disorders and dementia (HAD), collectively called neuroAIDS. At present, neuroAIDS develops in 30-50% HIV-seropositive (HIV+) patients, and represents a serious concern in clinical care for HIV-infected populations. The current diagnostic methods for neuroAIDS are based on measuring advanced clinical symptoms using neurological and psychological tests. There are no molecular tests for neuroAIDS, and not treatments other than HAART. There is an urgent need to better understand the molecular mechanism of neuroAIDS in order to develop new diagnostic and treatment strategies.

Brain autopsy samples were obtained from three cases of neuroAIDS (clinical dementia and post-mortem diagnosis of encephalitis) and two control cases (dementia and encephalitis free, age-matched AIDS). From each case, 3 anatomical areas of brain were sampled: (1) frontal cortex, (2) basal ganglia and (3) cerebellum. The expression of a panel of 41 SR biomarkers was analyzed in the brain samples using methods described in Example 5. The control samples were used to define baseline expression levels. HIV infection was detected using a mouse monoclonal IgG1 to recombinant HIVp24gag protein (Kal-1, Dako). Microglia/macrophages (positive control) were detected using a mouse monoclonal IgG1 to human CD 68 (KP-1, Dako).

Numerous HIV infected macrophages/microglial cells were detected in frontal cortex and basal ganglia, but not in cerebellum, in all three neuroAIDS samples. No HIV infected cells were found in control samples. A similar pattern of HIV infection in neuroAIDS was reported previously.

To rapidly survey stress levels, a combined SR biomarker assay was used to measure the combined levels of all 41 SR biomarkers. SR biomarker expression was found in multiple cell types: neurons, glia, microglia/macrophages and in the neuro-epithelium. The neuroAIDS samples had 10-80 fold higher levels of the combined SR biomarkers than the control samples. The levels were highest in frontal cortex and basal ganglia indicating that stress in these anatomical areas was more severe than in cerebellum. These results show that cellular stress is widespread in the brain of neuroAIDS patients and is present in infected as well as uninfected cell types and anatomical areas.

To gain a detailed insight into the distribution of SR biomarker expression in specific micro-anatomical areas (white matter, gray matter) and specific cell types (macrophages/microglia in white matter and neurons/glia in grey matter), computerized image analysis was performed as described in Example 1. Results for a representative SR biomarker (beta-endorphin) showed that the biomarker level in frontal cortex was 75-fold higher in neuroAIDS than in controls. The increased SR biomarker was preferentially found in white matter (96-fold increase) as compared to grey matter (7-fold increase). Within white matter, the SR biomarker was localized to perivascular inflammatory cell clusters. Within grey matter, the SR biomarker was localized to neurons and glia.

To classify stress in neuroAIDS, SR profiles in the brain samples were compared with the SR profiles in the reference skin samples, using methods shown in Example 5. The neuroAIDS samples were classified as stressed, and the control samples as normal, by both the 40 and the 5 SR biomarker panels. SR profiles of frontal cortex and basal ganglia in all three neuroAIDS cases were similar and distinct from SR profiles of neuroAIDS cerebellum.

SR pathway profiling analysis was applied to analyze the molecular mechanism of stress using the same methods as in Example 5. The variability of SR pathways is in Table 10 below.

TABLE 10

Variability of SR Pathways in NeuroAIDS

| | SR Pathway | Variability Index |
|---|---|---|
| 1 | Redox | 0.96 |
| 2 | Xenobiotics | 0.99 |
| 3 | Chaperoning | 0.96 |
| 4 | DNA repair | 0.88 |
| 5 | Cell adhesion | 0.83 |
| 6 | Cell growth | 0.88 |
| 7 | Cell death | 0.91 |
| 8 | NE signaling | 0.82 |
| 9 | Immunity | 0.83 |
| 10 | Microbial activation | 0.91 |

It was found that pathways 1, 2 and 3 were most activated indicating that the molecular mechanism of neuroAIDS-related stress involves increased free radicals (the trigger for pathway 1), increased levels of toxic molecules (the trigger for pathway 2) and misfolded proteins (the trigger for pathway 3). SR pathway variability was higher in frontal cortex and basal ganglia providing further evidence that cellular stress was more severe in these brain areas than in cerebellum.

In conclusion, it was demonstrated that the SR profiling methods and the SR biomarker panels constructed using the reference skin samples, are directly applicable to brain samples and relevant to neuroAIDS. These results provide new information into the cellular and molecular mechanisms of neuroAIDS, which might be useful for the development of new diagnostic approaches to neuroAIDS (no laboratory test is currently available), and in designing and monitoring neuroAIDS treatment.

Example 8

SR Biomarker Assays for Saliva-Based Analysis of Psychological Trauma

Psychological trauma is common and can cause debilitating health disorders such as the post-traumatic stress disorder (PTSD). Current diagnostic methods for MD are based on neurological and psychological tests that are laborious and not suitable for early diagnostics of PTSD. There is no laboratory test for PTSD.

Longitudinal saliva samples (about 0.1 ml, 20 time points) were obtained from four healthy volunteers by passive drooling into a test tube. Another volunteer was sampled in the same way before and during a two-month-long psychological trauma related to a grieving process (8 time points). The saliva samples were used to prepare alcohol-fixed cell smears on histology slides. The saliva samples were analyzed using the SR biomarker pool assay described in Example 4. The samples obtained from the healthy volunteers were used to define baseline scores. Cytokeratin (positive control) was analyzed in parallel.

The SR biomarker pool scores in all control samples were near baseline and showed a low fluctuation indicating that the baseline was stable. The other volunteer also had baseline scores before the psychological trauma. The scores in that volunteer started to rise after the psychological trauma (about 10-fold increase), reached the highest levels in about 2 weeks after the trauma (about 100-fold increase) and declined to near baseline level on in a month and half.

In conclusion, this Example documents that stress response profiling is suitable for saliva samples and relevant to stress related to psychological trauma, and the results are useful for monitoring stress levels and the time course of stress.

Example 9

SR Profiling for the Analysis of Stress in Massaged and Diseased Skin

Skin massage has been historically used to reduce stress. Massaging is frequently performed but the underlying molecular mechanisms, including the stress-reducing effects, are little understood. To analyze the effects of massage, SR biomarkers were assayed in normal skin before and after massage, and in diseased skin that served as a positive control for stress.

Skin biopsy samples were obtained from 7 subjects: 4 controls (healthy volunteers), one healthy volunteer before and after a professional therapeutic skin massage, and two psoriasis patients. The expression of a panel of 41 SR biomarkers was analyzed in the skin samples using methods described in Example 5.

The combined levels of the 41 biomarkers, measured using the combined SR biomarker assay, were 13-fold higher in psoriasis than in healthy skin, and 3-fold higher in the massaged skin.

The massage decreased the expression of 22 SR biomarkers and increased the expression of 7 biomarkers indicating that the dominant effect of the massage was a downregulation of stress responses. This effect was opposite to the upregulation of diverse stressors (see Examples 1-8.)

The variability index for the SR pathways is in Table 11 below:

TABLE 11

Variability of SR Pathways in Massage and Psoriasis

| | SR Pathway | Variability index | |
| | | Massage | Psoriasis |
|---|---|---|---|
| 1 | Redox | 0.579 | 0.898 |
| 2 | Xenobiotics | 0.497 | 0.965 |
| 3 | Chaperoning | 0.189 | 1.029 |
| 4 | DNA repair | 2.085 | 0.847 |
| 5 | Cell adhesion | 1.052 | 1.003 |
| 6 | Cell growth | 0.321 | 0.968 |
| 7 | Cell death | 0.461 | 0.822 |
| 8 | NE signaling | 0.519 | 0.902 |
| 9 | Immunity | 0.581 | 0.999 |
| 10 | Microbial activation | 1.165 | 0.644 |

All pathways were downregulated by the massage. The most downregulated pathways were 4, 5 and 10 (DNA repair, cellular adhesion and motility, microbial activation.) In contrast, psoriasis-related stress upregulated SR pathway activity, in particular pathways 3, 5 and 9 indicating increased levels of misfolded proteins (the trigger for pathway 3), changes in cellular adhesion and motility (the trigger for pathway 5) and increased stimulation of immune responses (the trigger for pathway 9).

In conclusion, this experiment demonstrated that SR profiling and the SR biomarker panels constructed using the reference skin samples, are relevant to the analysis of stress modulation by stress-relieving treatments such as therapeutic skin massage. The results have practical applications for the development of noninvasive tests for monitoring of the effects of stress-relieving treatments including acupuncture and other modalities of complementary and alternative medicine.

Example 10

SR Profiling and Combined SR Biomarker Assays to Detect Disease in Elephants Wild elephants show increased incidence of disease outbreaks and aggressive behaviors suggesting an incipient health crisis. Current methods for assessing the health of a population are based on estimated trends in abundance, mortality, and reproductive rates. These methods are sometimes too slow to provide early warnings of compromised health in populations with long generation times, such as elephants.

SR biomarkers were applied to measure stress is elephants with known health status to evaluate whether stress measurements could be used to predict elephant health. Skin biopsies were obtained from two captive African elephants with clinically diagnosed gastrointestinal infection and from four healthy wild elephants from the Addo National Park in South Africa. The expression of a panel of 41 SR biomarkers was analyzed using methods described in Example 5.

To rapidly survey stress levels, the combined level of the 41 SR biomarkers were measured using the combined SR biomarker assay. The SR biomarker expression was consistently found in the epidermis of the elephant skin, as in the reference skin samples (Examples 1-4). The combined SR biomarker levels were 5 to 7-fold higher in the diseased samples than in the control.

To classify stress, SR profiles in elephants were compared to the reference SR profiles in the reference skin samples, using methods described in Example 5. The diseased elephants were classified as stressed and the healthy elephants as normal by both the 40 and the 5 SR biomarker panels.

SR profiling as described in Example 3 was applied to analyze the molecular mechanism of stress in elephants. The variability of SR pathways is in Table 12 below.

TABLE 12

Variability of SR Pathways in Elephant Disease

| | SR pathway | Variability Index |
|---|---|---|
| 1 | Redox | 0.677 |
| 2 | Xenobiotics | 0.673 |
| 3 | Chaperoning | 0.817 |
| 4 | DNA repair | 0.706 |
| 5 | Cell adhesion | 0.466 |
| 6 | Cell growth | 0.532 |
| 7 | Cell death | 0.511 |
| 8 | NE signaling | 0.547 |
| 9 | Immunity | 0.566 |
| 10 | Microbial activation | 0.585 |

Pathways 3 and 4 were most activated in the diseased elephants indicating that their molecular mechanism of stress mostly involved misfolded proteins (the trigger for pathway 3) and DNA mutations (the trigger for pathway 4).

In conclusion, it was demonstrated that SR profiling and the SR biomarker panels constructed using the reference skin samples, are directly applicable to elephant skin samples and relevant to elephant diseases. The results show that SR biomarker profiling is useful for predicting health in captive and wild elephants and may provide a starting point for practical applications in elephant conservation.

Example 11

SR Profiling for the Analysis of Stress in Cultured Human Cells

In vitro toxicity testing reveals the effects of toxic substances on cultured bacterial or mammalian cells. It is employed primarily to identify potentially hazardous chemical or biological agents and/or to confirm the lack of certain toxic properties in the early stages of the development of potentially useful new substances such as therapeutic drugs, agricultural chemicals and direct food additives. In vitro toxicity testing is a useful, time and cost-effective supplement to toxicology studies in living animals. In vitro assays for xenobiotic toxicity are recently carefully considered by key government agencies (e.g. the Environmental Protection Agency (EPA), the National Institute of Environmental Health Sciences/National Toxicity Program (NIEHS/NTP), and the Food and Drug Administration (FDA)) in order to reduce the use of animals in research, and to advance mechanistic understanding of toxicant activities.

There is a particular interest in toxicity testing based on human cells that might define human-specific toxic effects. Current methods include the detection of changes in cellular morphology using electron microscopy and image analysis, cell death (apoptosis) assays and cellular transformation (cancer) assays. These assays are laborious and do not provide early warnings of the initial molecular damage in the cell that may be an important indicator of compromised cellular health, before the emergence of observable changes in cellular morphology or the onset of cellular transformation or apoptosis. To systematically monitor early molecular changes in cultured cells exposed to chemical or biological agents, the 41 SR biomarker panel was queried using methods described in Example 5.

Samples were primary cultures of human epithelial cells from gut and tonsils cultured on multichamber microscopy slides. Cells were treated with chemical stressors including alloxan (oxidizing agent and DNA mutagen) or with physical stressors including heat shock and uv light, or with biological stressors including the infection with disease-causing viruses (HTLV-1, HIV) or bacteria (Streptococcus pyogenes). Control cells were cultured for the same time as treated cells, without any treatments. At the end of treatments, adherent cells were fixed in situ using 10% normal buffered formalin. The combined levels of the 41 SR biomarkers were measured using the combined SR biomarker assay. The combined levels were increased 3 to 30 fold by the treatments.

In conclusion, it was demonstrated that the SR profiling and the SR biomarker panels constructed using the reference skin samples, are directly applicable to samples of cultured human cells and relevant to diverse physical, chemical and biological stressors. The results have practical applications in in vitro toxicity testing.

With respect to ranges of values, the invention encompasses each intervening value between the upper and lower limits of the range to at least a tenth of the lower limit's unit, unless the context clearly indicates otherwise. Moreover, the invention encompasses any other stated intervening values and ranges including either or both of the upper and lower limits of the range, unless specifically excluded from the stated range.

Unless defined otherwise, the meanings of all technical and scientific terms used herein are those commonly understood by one of ordinary skill in the art to which this invention belongs. One of ordinary skill in the art will also appreciate that any methods and materials similar or equivalent to those described herein can also be used to practice or test this invention.

The publications and patents discussed herein are provided solely for their disclosure prior to the filing date of the present application. Nothing herein is to be construed as an admission that the present invention is not entitled to antedate such publication by virtue of prior invention. Further the dates of publication provided may be different from the actual publication dates which may need to be independently confirmed.

All the publications cited are incorporated herein by reference in their entireties, including all published patents, patent applications, literature references, as well as those publications that have been incorporated in those published documents. However, to the extent that any publication incorporated herein by reference refers to information to be published, applicants do not admit that any such information published after the filing date of this application to be prior art.

As used in this specification and in the appended claims, the singular forms include the plural forms. For example the terms "a," "an," and "the" include plural references unless the content clearly dictates otherwise. Additionally, the term "at least" preceding a series of elements is to be understood as referring to every element in the series. The inventions illustratively described herein can suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the future shown and described or any portion thereof, and it is recognized that various modifications are possible within the scope of the invention claimed.

Thus, it should be understood that although the present invention has been specifically disclosed by preferred embodiments and optional features, modification and variation of the inventions herein disclosed can be resorted by those skilled in the art, and that such modifications and variations are considered to be within the scope of the inventions disclosed herein. The inventions have been described broadly and generically herein. Each of the narrower species and subgeneric groupings falling within the scope of the generic disclosure also form part of these inventions. This includes the generic description of each invention with a proviso or negative limitation removing any subject matter from the genus, regardless of whether or not the excised materials specifically resided therein. In addition, where features or aspects of an invention are described in terms of the Markush group, those schooled in the art will recognize that the invention is also thereby described in terms of any individual member or subgroup of members of the Markush group.

It is also to be understood that the above description is intended to be illustrative and not restrictive. Many embodiments will be apparent to those of in the art upon reviewing the above description. The scope of the invention should therefore, be determined not with reference to the above description, but should instead be determined with reference to the appended claims, along with the full scope of equivalents to which such claims are entitled. Those skilled in the art will recognize, or will be able to ascertain using no more than routine experimentation, many equivalents to the specific embodiments of the invention described. Such equivalents are intended to be encompassed by the following claims.

I claim:

1. A method for constructing a stress response (SR) pathway profile for a subject, comprising:
   (i) constructing a panel of at least 3 stress response (SR) biomarkers;
   (ii) obtaining a biological sample from the subject containing the SR biomarkers in the panel;
   (iii) determining quantitative immunochemical measurements of the SR biomarkers in the panel by computerized image analysis of staining intensity (SI);
   (iv) calculating biomarker scores of the SR biomarkers in the panel based on the staining intensity, wherein a score of 0 represents a baseline score for a normal control; and
   (v) calculating a pathway profile score (Z) from the biomarker scores according to an equation of Formula I:

$$Z = \begin{bmatrix} Z_1 \\ \vdots \\ Z_{10} \end{bmatrix} \approx \begin{matrix} Z_1 = f_{1,1}y_1 + f_{1,2}y_2 + \ldots + f_{1,40}y_{40} \\ \vdots \\ Z_{10} = f_{2,1} + f_{2,2}y_2 + \ldots + f_{2,40}y_{40} \end{matrix}$$

or $$Z_{p,i} = \sum_{p=1}^{10} \sum_{i=1}^{40} f_{pi} y_i$$

where;
Z is a SR pathway profile;
$Z_p$ is the SR pathway profile for the p-th pathway, p=1, ..., 10;
$y_i$ is the i-th SR biomarker's score, i=1, ..., 40; and
$f_{pi}$ is a is a constant that indicates the relatedness between the p-th SR pathway and the i-th SR biomarker;
   (vi) comparing the pathway profile score from the sample to the pathway profile score of normal control, wherein pathways having a difference in score in the sample as compared to the normal control are included in an SR pathway profile.

2. The method according to claim 1, wherein the profile includes a sufficient number of SR biomarkers to differentiate between the sample and the normal control to a preselected reliability level.

3. The method according to claim 1, wherein the preselected reliability level is 90% or greater.

4. The method according to claim 1, wherein the preselected reliability level is 75% or greater.

5. The method according to claim 1, wherein the SR biomarker panel consists of SR biomarkers selected from the group consisting of β-endorphin, caspase 8, cyclin D1, cyclooxygenase 2, cytochrome P450, cytoplasmic cytochrome C, epidermal growth factor receptor, ferritin, glucocorticoid receptor, glucose regulated protein Grp58, glucose regulated protein Grp75, glutathione S-transferase π, heat shock protein 25/27, heat shock protein 40, heat shock protein 60, heat shock protein 70, heat shock protein 90, heat shock transcription factor HSF-1, heme oxygenase-1, interleukin IL-1β, interleukin IL-6, interleukin IL-8, interleukin IL-10, interleukin IL-12, laminin, leptin receptor, metallothionein, stress-activated MAP kinase Mekk-1, mitogen-activated MAP kinase Mek-1, NADPH-cytochrome P450 reductase, inducible nitric oxide synthase H, proto-oncogene c-Fos protein, proto-oncogene c-Jun protein, serotonin receptor, serotonin, substance P, superoxide dismutase Mn, superoxide dismutase Cu/Zn, transforming growth factor β, tumor suppressor p53 and vasoactive intestinal peptide.

6. The method of claim 1, further comprising determining a variability index for the biomarker scores by calculating the variability of biomarker scores from the subject as compared to a normal control according to an equation of Formula II:

$$v_i = l_{1i}x_{1i} + l_{2i}x_{2i} \quad (II)$$

where;
$v_i$ is the variability index for the i-th SR biomarker (i=1, ..., 40); and
$l_{1i}$ and $l_{2i}$ are the pc1 and pc2 eigenvalues for the i-th SR biomarker; and
$x_{1i}$ and $x_{2i}$ are the absolute values of pc1 and pc2 eigenvectors for the i-th SR biomarker.

7. The method of claim 1, further comprising determining a variability index for the SR pathways by calculating the variability of SR pathways scores from the sample as compared to a normal control according to an equation of Formula III:

$$v_p = l_{1p}x_{1p} + l_{2p}x_{2p} \quad (III)$$

where;
$v_p$ is the variability index for the p-th pathway (i=1, ..., 10);
$l_{1p}$ and $l_{2p}$ are the pc1 and pc2 eigenvalues for the p-th pathway; and
$x_{1p}$ and $x_{2p}$ are the pc1 and pc2 eigenvectors for the p-th pathway.

8. The method of claim 1, further comprising clustering the SR pathway profile scores of the sample utilizing multivariate statistics, wherein separate clustering of the sample as compared to the normal control is indicative of a disease or disorder.

* * * * *